US 6,686,339 B1

United States Patent
Murdin et al.

(10) Patent No.: US 6,686,339 B1
(45) Date of Patent: Feb. 3, 2004

(54) NUCLEIC ACID MOLECULES ENCODING INCLUSION MEMBRANE PROTEIN C OF CHLAMYDIA

(75) Inventors: Andrew D. Murdin, Newmarket (CA); Pamela L. Dunn, Mississauga (CA); Raymond P. Oomen, Schomberg (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/763,063

(22) PCT Filed: Aug. 19, 1999

(86) PCT No.: PCT/CA99/00766

§ 371 (c)(1),
(2), (4) Date: Jun. 15, 2001

(87) PCT Pub. No.: WO00/11181

PCT Pub. Date: Mar. 2, 2000

Related U.S. Application Data

(60) Provisional application No. 60/097,199, filed on Aug. 20, 1998, and provisional application No. 60/132,961, filed on May 7, 1999.

(51) Int. Cl.[7] .................. A61K 48/00; A61K 35/66; C12N 15/63; C07H 21/04
(52) U.S. Cl. ............ 514/44; 435/320.1; 536/23.1; 536/23.2; 536/24.1; 424/93.2
(58) Field of Search ............ 514/44; 435/320.1; 536/23.1, 23.2, 24.1; 424/93.2

(56) References Cited

U.S. PATENT DOCUMENTS

| | | | |
|---|---|---|---|
| 4,722,848 A | 2/1988 | Paoletti et al. | 424/89 |
| 4,882,278 A | 11/1989 | Mekalanos | 435/172.3 |
| 4,920,209 A | 4/1990 | Davis et al. | 435/235 |
| 4,945,050 A | 7/1990 | Sanford et al. | 435/172.1 |
| 4,952,496 A | 8/1990 | Studier et al. | 435/91 |
| 5,015,580 A | 5/1991 | Christou et al. | 435/172.3 |
| 5,028,530 A | 7/1991 | Lai et al. | 435/69.1 |
| 5,057,546 A | 10/1991 | Sudan | 521/107 |
| 5,283,185 A | 2/1994 | Epand et al. | 435/172.3 |
| 5,364,773 A | 11/1994 | Paoletti et al. | 435/69.1 |
| 5,527,928 A | 6/1996 | Nantz et al. | 554/105 |

FOREIGN PATENT DOCUMENTS

| | | |
|---|---|---|
| EP | 187702 | 7/1986 |
| WO | WO 88/06626 | 9/1988 |
| WO | WO 88/09336 | 12/1988 |
| WO | WO 90/00594 | 1/1990 |
| WO | WO 90/11092 | 10/1990 |
| WO | WO 91/00359 | 1/1991 |
| WO | WO 91/13157 | 9/1991 |
| WO | WO 91/15501 | 10/1991 |
| WO | WO 92/01796 | 2/1992 |
| WO | WO 92/11354 | 7/1992 |
| WO | WO 92/11361 | 7/1992 |
| WO | WO 92/21376 | 10/1992 |
| WO | WO 93/17706 | 9/1993 |
| WO | WO 93/18759 | 9/1993 |
| WO | WO 93/19768 | 10/1993 |
| WO | WO 94/01533 | 1/1994 |
| WO | WO 94/16737 | 8/1994 |
| WO | WO 94/19482 | 9/1994 |
| WO | WO 94/21797 | 9/1994 |
| WO | WO 94/24263 | 10/1994 |
| WO | WO 94/25608 | 11/1994 |
| WO | WO 95/02397 | 1/1995 |
| WO | WO 95/17211 | 6/1995 |
| WO | WO 95/26356 | 10/1995 |
| WO | WO 96/06627 | 3/1996 |
| WO | WO 96/14831 | 5/1996 |
| WO | WO 99/27105 | 6/1999 |

OTHER PUBLICATIONS

Bachmaier et al., Chlamydia infections and heart disease linked through antigenic mimicry, 1999, Science, vol. 283, pp. 1335–1339.*
Ertl et al., Genetic immunization, 1996, Viral Immunology, vol. 9, pp. 1–9.*
Monteil et al., Genetic immunization of seronegative one–day–old piglets against pseudorabies induces neutralizing antibodies but not protection and is ineffective in piglets from immune dams, 1996, Vet. Res., vol. 27, pp. 443–452.*
Yasutomi et al., A vaccine–elicited, single viral epitope–specific cytotoxic T lymphocyte response does not protect against intravenous, cell–free immunodeficiency virus challenge, 1995, Journal of Virology, pp. 2279–2284.*
Puolakkainen et al. Further characterization of *Chlamydia pneumoniae* specific monoclonal antibodies. Microbiol Immunol. 1995;39(8):551–4.*
Harlow and Lane, "Antibodies: a laboratory manual", 1998, Cold Spring Harbor Laboratory.*
Grayston et al. (1995), Journal of Infectious Diseases 168:1231–1235.
Campos et al. (1995), Investigation of Ophthalmology and Visual Science 36:1477–1491.
Grayston et al (1990), Journal of Infectious Diseases 161:618–625.
Marrie (1993), Clinical Infectious Diseases. 18:501–515.
Wang et al (1986), Chlamydial Infections. Cambridge University Press, Cambridge, p. 329–332.
Normann et al., Acta Paediatrica, 1988, vol. 87, Iss 1, pp 23–27.
Saikku et al.(1988), Lancet:983–985.
Thom et al. (1992), JAMA 268:68–72.
Linnanmaki et al. (1993), Circulation 87:1030–1034.
Saikku et al. (1992), Annals Internal Medicine 116:273–278.

(List continued on next page.)

Primary Examiner—James Ketter
Assistant Examiner—Daniel M. Sullivan

(57) ABSTRACT

In summary of this disclosure, the present invention provides a method of nucleic acid, including DNA, immunization of a host, including humans, against disease caused by infection by a strain of Chlamydia, specifically *C. pneumoniae*, employing a vector, containing a nucleotide sequence encoding a inclusion membrane protein C of a strain of *Chlamydia pneumoniae* and a promoter to effect expression of the inclusion membrane protein C gene in the host. Modifications are possible within the scope of this invention.

38 Claims, 12 Drawing Sheets

OTHER PUBLICATIONS

Melnick et al(1993), American Journal of Medicine 95:499–504.
Shor et al. (1992), South African. Medical Journal 82:158–161.
Kuo et al. (1993), Journal of Infectious Diseases 167:841–849.
Kuo et al. (1993), Arteriosclerosis and Thrombosis 13:1500–1504.
Campbell et al (1995), Journal of Infectious Diseases 172:585–588.
Chiu et al. Circulation, 1997 96(7);2144–2148.
Ramirez et al (1996) Annals of Internal Medicine 125:979–982.
Jackson et al. Abst. K121, p272, 36th ICAAC, Sep. 15–18, 1996, New Orleans.
Fong et al (1997) Journal of Clinical Microbiology 35:48–52.
Hahn DL et al. Evidence for *Chlamydia pneumoniae* infection in steroid–dependent asthma. Ann Allergy Asthma Immunol. Jan. 1998; 80(1):45–49.
Hahn DL, et al. Association of *Chlamydia pneumoniae* IgA antibodies with recently symptomatic asthma. Epidemiol Infect. Dec. 1996; 117(3): 513–517.
Bjornsson E, et al. Serology of chlamydia in relation to asthma and bronchial hyperresponsiveness. Scand J Infect Dis. 1996; 28(1): 63–69.
Hahn DL. Treatment of *Chlamydia pneumoniae* infection in adult asthma: a before–after trial. J Fam Pract. Oct. 1995; 41(4): 345–351.
Allegra L, et al. Acute exacerbations of asthma in adults: role of *Chlamydia pneumoniae* infection. Eur Respir J. Dec. 1994; 7(12): 2165–2168.
Hahn DL, et al. Association of *Chlamydia pneumoniae* (strain TWAR) infection with wheezing, asthmatic bronchitis, and adult–onset asthma. JAMA. Jul. 10, 1991; 266(2): 225–230.
Pal et al.(1996) Infection and Immunity.64:5341–5348.
Jones et al. (1995) Vaccine 13:715.
Igietseme et al, (1993) Immunology 5:317 (See #29 below).
Igietseme et al (1993) Regional Immunology 5:317.
Magee et al (1993) Regional Immunology 5: 305–311.
Landers et al (1991) Infection & Immunity 59:3774–3777.
Magee et al (1995) Infection & Immunity 63:516–521.
Cotter et al. (1995) Infection and Immunity 63:4704–4714.
Campbell et al (1990) Infection and Immunity 58:93–97.
McCafferty et al (1995) Infection and Immunity 63:2387–2389.
Knudsen et al (1996)Third Meeting of the European Society for Chlamydia Research, Vienna.
Wiedmann–Al–Ahmad M, et al. Reactions of polyclonal and neutralizing anti–p54 monoclonal antibodies with an isolated, species–specific 54–kilodalton protein of *Chlamydia pneumoniae*. Clin Diagn Lab Immunol. Nov. 1997; 4(6): 700–704.
Hughes et al., 1992. Infect. Immun. 60(9):3497–3503.
Dion et al., 1990. Virology 179:474–477.
Snijders et al., 1991. J. Gen. Virol. 72:557–565.
Langeveld et al., Vaccine 12(15):1473–1480, 1994.
Ausubel et al., Current Protocols in Molecular Biology, John Wiley & Sons Inc., 1994.
Kunkel et al. Proc. Natl. Acad. Sci. USA (1985) 82:448–492.
Silhavy et al. Experiments with Gene Fusions, Cold Spring Harbor Laboratory Press, 1984.
Davis et al. A Manual for Genetic Engineering: Advanced Bacterial Genetics, Cold Spring Harbor Laboratory Press, 1980).
Casey & Davidson, Nucl. Acid Res. (1977) 4:1539–1553.
Cagnon et al., Protein Engineering (1991) 4(7):843–847.
Takase et al., J. Bact. (1987) 169:5692–5699.
Perez Melgosa et al., Infect Immun (1994) 62:880–886.
Watson et al., Nucleic Acids Res (1990) 18:5299.
Watson et al., Microbiology (1995) 141:2489–2497.
Melgosa et al., FEMS Microbiol Lett (1993) 112:199–204.
Campbell et al., J Clin Microbiol (1990) 28 :1261.1264.
Iijima et al., J Clin Microbiol (1994) 32:583.–588.
Tartaglia et al, Virology (1992) 188:217–232.
Taylor et al, Vaccine (1995) 15:359.
Kieny et al., Nature (1994) 312:163.
Mekalanos et al., Nature (1983) 306:551–557.
Nakayama et al., Bio/Tech. (1988) 6:693–697.
High et al., EMBO (1992) 11:1991–1999.
Sizemore et al., Science (1995) 270:299–302.
Medaglini et al., Pro. Natl. Acad. Sci. USA (1995) 92:6868–6872.
Flynn J.L., Cell. Mol. Biol. (1994) 40 (suppl.I):31–36.
Norton & Coffin, Molec. Cell Biol. (1985) 5:281–290.
Li et al., Gene (1989) 78:243–254.
Li & Paulin, J. Biol. Chem. (1991) 266:6562–6570.
Li & Paulin, J. Biol. Chem. (1993) 268:10403–10415.
Hartikka et al., Human Gene Therapy (1996) 7:1205–1217.
Tang et al., Nature (1992) 356:152–154.
Davis et al., Vaccine 1994, 12:1503–1509.
Nielsen et al., Science (1991) 254:1497–1500.
Southern, J. Mol. Biol. (1975) 98:503–517.
Dunn et al., Cell (1977) 12:23–36.
Towbin et al., Proc. Natl. Acad. Sci. USA (1779) 76:4350–4354.
Laemmli, Nature (1970) 227:680–685.
Bachmaier et al., Science (1999) 283:1335–1338.
Yang et al., 1993, Infection & Immunity, vol. 61, pp 2037–40.
Chi E.Y., Kuo C.C., Grayston J.T., 1987. Unique ultrastructure in the elementary body of Chlamydia sp strain TWAR. J. Bacteriol 169(8): 3757–63.
Needleman, S.B., and Wunsch, C.D. 1970, J. Mol. Biol. 48:443–453.
Sellers, P.H. 1974 On the theory and computation of evolutionary distances. J. Appl. Math (Siam) 26:787–793.
Waterman, M.S., Smith, T.F., and Beyer, W.A. 1976. Advan. Math. 20:367–387.
Smith, T.F., and Waterman, M.S. 1981 Identification of common molecular subsequences. J. Mol. Biol. 147:195–197.
Sobel, E. and Martinez, H.M. 1985 A Multiple Sequence Alignment Program. Nucleic Acids Res. 14:363–374.
Chapman S. B et al Nucleic Acid Research, vol. 19, No. 14 3979–3986.
Bannantine J.P., Rockey D.D., Hackstandt T. Molecular Microbiology (1998) 28(5), 1017–1026.
Gaydos, A.C., Quinn T.C., BoBo D.L. Eiden J.J., Infection and Immnityy (1992), p. 5319–5323.
Promega "1997 Promega Catalog" p. 136.
Invitrogen: "1997 Product Catalog" p. 45.
Batein N. et al Vaccine vol. 15. No. 12/13 pp. 1385–1390 (1997).

* cited by examiner

FIG.1A

Sequence of *C. pneumoniae* inclusion membrane protein C gene.

```
aactctctaa ttaaaccgt aattactgtc cgtacaacaa gataataagt aaaaaacaca  60
aaaaatagtg atttt atg acc tca ccg atc ccc ttt cag tct agt ggc gat  111
              Met Thr Ser Pro Ile Pro Phe Gln Ser Ser Gly Asp
                1                   5                        10 gcc tct ttc ctt gcc gag cag cca cag caa ctc ccg tct act tct gaa  159
Ala Ser Phe Leu Ala Glu Gln Pro Gln Gln Leu Pro Ser Thr Ser Glu
         15                      20                      25 tct cag cta gta act caa ttg cta acc atg atg aag cat act caa gca  207
Ser Gln Leu Val Thr Gln Leu Leu Thr Met Met Lys His Thr Gln Ala
         30                      35                      40 tta tcc gaa acg gtt ctt caa caa cgc gat cga tta cca acc gca      255
Leu Ser Glu Thr Val Leu Gln Gln Arg Asp Arg Leu Pro Thr Ala
         45                      50                      55    60 tct att atc ctt caa gta gga gct cct aca gga gga gcg ggt gcg      303
Ser Ile Ile Leu Gln Val Gly Ala Pro Thr Gly Gly Ala Gly Ala
         65                      70                           75
```

FIG.1B

```
cct ttt caa cca gga ccg gca gat gat cat cat ccc ata ccg ccg    351
Pro Phe Gln Pro Gly Pro Ala Asp Asp His His Pro Ile Pro Pro
         80                      85                      90 cct gtt gta cca gct caa ata gaa aca gaa atc acc act ata aga tcc    399
Pro Val Val Pro Ala Gln Ile Glu Thr Glu Ile Thr Thr Ile Arg Ser
         95                     100                     105 gag tta cag ctc atg cga tct act cta caa caa agc aca aaa gga gct    447
Glu Leu Gln Leu Met Arg Ser Thr Leu Gln Gln Ser Thr Lys Gly Ala
        110                     115                     120 cgt aca gga gtt cta gtg gtt act gca atc tta atg acg atc tcc tta    495
Arg Thr Gly Val Leu Val Val Thr Ala Ile Leu Met Thr Ile Ser Leu
        125                     130                     135                     140 ttg gct att att atc ata ata cta gct gtg ctt gga ttt acg ggc gtc    543
Leu Ala Ile Ile Ile Ile Ile Leu Ala Val Leu Gly Phe Thr Gly Val
        145                     150                     155 ttg cct caa gta gct tta ttg atg cag ggt gaa aca aat ctg att tgg    591
Leu Pro Gln Val Ala Leu Leu Met Gln Gly Glu Thr Asn Leu Ile Trp
        160                     165                     170
```

FIG.1C

```
gct atg gtg agc ggt tct att att att tgc ttt att gcg cta att gga act   639
Ala Met Val Ser Gly Ser Ile Ile Ile Cys Phe Ile Ala Leu Ile Gly Thr
            175                 180                 185 cta gga tta att tta aca aat aag aac acg cct cta ccg gct tct           684
Leu Gly Leu Ile Leu Thr Asn Lys Asn Thr Pro Leu Pro Ala Ser
            190                 195                 200 taaaaaata aattgaatta gaataagtaa tagtaatttt cttcatacct cccttgcaat      744
taatca                                                                750
```

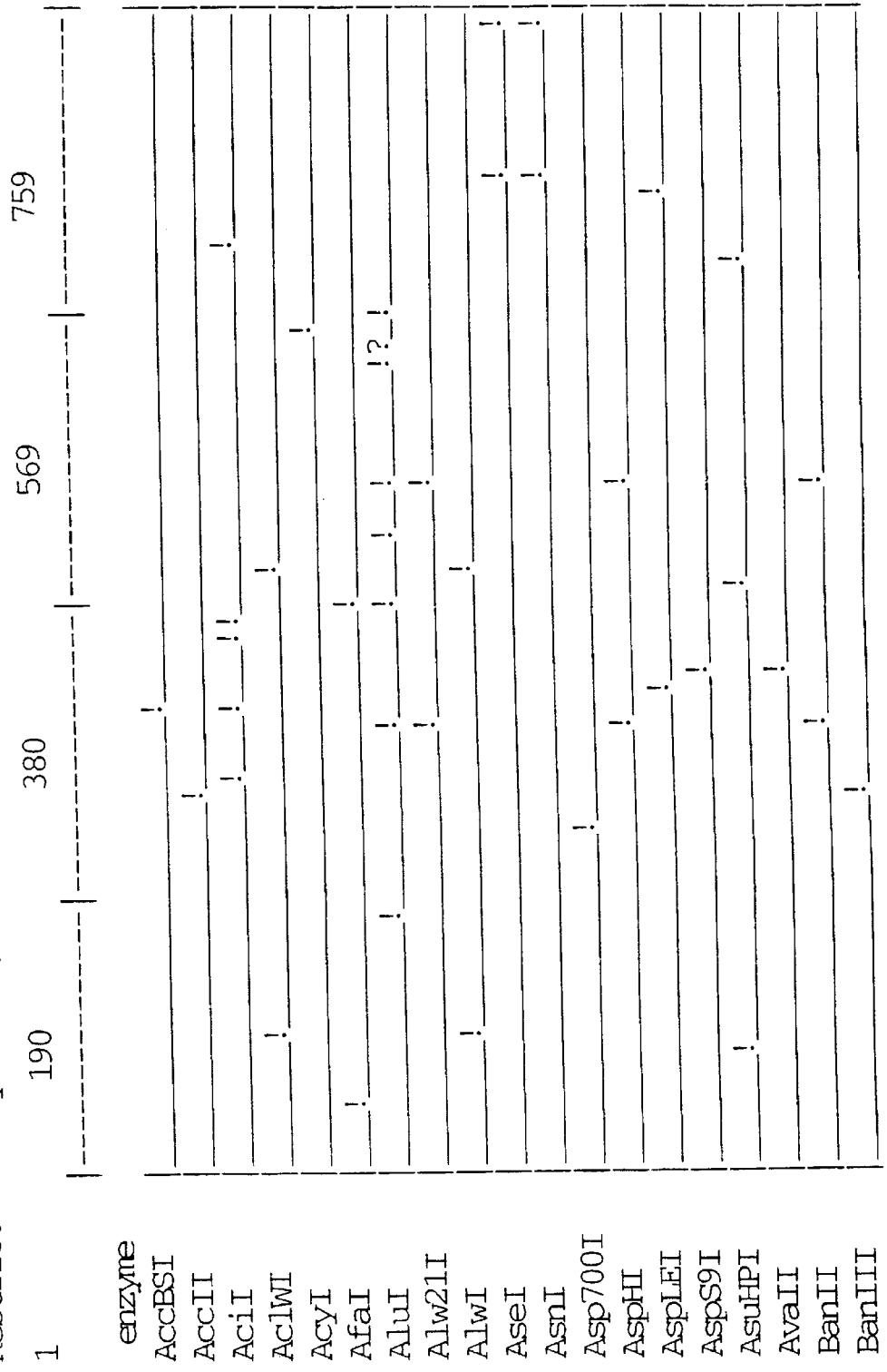

FIG.2B

BbiII
Bbv12I
BbvI
BclI
BfaI
BfmI
Bme18I
BmyI
Bsa29I
BsaBI
BsaHI
BsaOI
Bsc4I
BscI
Bse118I
Bse8I
BseCI
BseRI
Bsh1236I
Bsh1285I
Bsh1365I
BsiBI
BsiEI
BsiHKAI

FIG.2C

BsiLI
BsiQI
BsiSI
BsiYI
BsiZI
BslI
Bsp106I
Bsp1286I
Bsp143II
BspXI
BsrBI
BsrBRI
BsrFI
BssAI
Bst2UI
Bst71I
BstACI
BstDEI
BstH2I
BstMCI
BstOI
BstSFI
BstUI
BstX2I

FIG.2D

BstYI
Bsu15I
Cfr10I
Cfr13I
ClaI
CviJI
DdeI
DpnI
Eco24I
Eco47I
EcoNI
EcoRII
EcoT38I
FauI
FbaI
Fmu4HI
FokI
Fri0I
Fsp4HI
HaeII
HapII
HgaI
HgiEI
HhaI

FIG.2F

MunI
MvnI
MwoI
NlaIII
Ple19I
PshBI
Psp124BI
PvuI
RsaI
SacI
Sau96I
ScrFI
SduI
SfaNI
SfcI
Sse9I
TaiI
TaqI
TfiI
ThaI
TruII
Tru9I
TscI
TseI

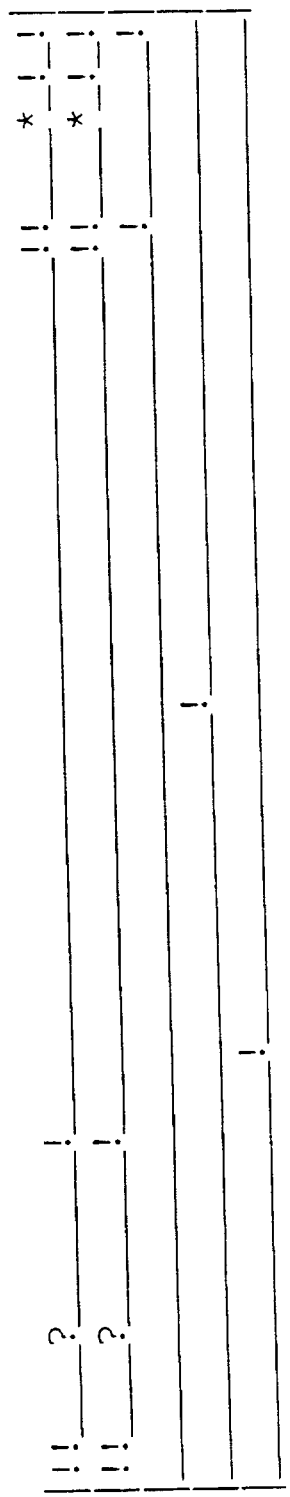

NUCLEIC ACID MOLECULES ENCODING INCLUSION MEMBRANE PROTEIN C OF CHLAMYDIA

REFERENCE TO RELATED APPLICATIONS

This application is a national phase application under 35 U.S.C. 371 of PCT/CA99/00766 filed Aug. 19, 1999 and claims benefit of U.S. provisional applications No. 60/132,961 filed May 7, 1999 and No. 60/097,199 filed Aug. 20, 1998.

FIELD OF INVENTION

The present invention relates to Chlamydia antigens and corresponding DNA molecules, which can be used in methods to prevent and treat Chlamydia infection in mammals, such as humans.

BACKGROUND OF THE INVENTION

Chlamydiae are prokaryotes. They exhibit morphologic and structural similarities to gram-negative bacteria including a trilaminar outer membrane, which contains lipopolysaccharide and several membrane proteins that are structurally and functionally analogous to proteins found in *E coli*. Chlamydiae are differentiated from other bacteria by their morphology and by a unique developmental cycle. They are obligate intra-cellular parasites with a unique biphasic life cycle consisting of a metabolically inactive but infectious extracellular stage and a replicating but non-infectious intracellular stage. The replicative stage of the life-cycle takes place within a membrane-bound inclusion which sequesters the bacteria away from the cytoplasm of the infected host cell.

Because chlamydiae are small and multiply only within susceptible cells, they were long thought to be viruses. However, they have many characteristics in common with other bacteria: (1) they contain both DNA and RNA, (2) they divide by binary fission, (3) their cell envelopes resemble those of other gram-negative bacteria, (4) they contain ribosomes similar to those of other bacteria, and (5) they are susceptible to various antibiotics. Chlamydiae can be seen in the light microscope, and the genome is about one-third the size of the *Escherichia coli* genome.

Many different strains of chlamydiae have been isolated from birds, man and other mammals, and these strains can be distinguished on the basis of host range, virulence, pathogenesis, and antigenic composition. There is strong homology of DNA within each species, but surprisingly little between species, suggesting long-standing evolutionary separation.

*C. trachomitis* has a high degree of host specificity, being almost completely limited to man, and causes ocular and genitourinary infections of widely varying severity. In contrast, *C. psittaci* strains are rare in man but are found in a wide range of birds and also in wild, domestic, and laboratory mammals, where they multiply in cells of many organs.

*C. pneumoniae* is a common human pathogen, originally described as the TWAR strain of *Chlamydia psittaci*, but subsequently recognised to be a new species. *C. pneumoniae* is antigenically, genetically and morphologically distinct from other Chlamydia species (*C. trachomitis, C. pecorum* and *C. psittaci*). It shows 10% or less DNA sequence homology with either of *C.trachomatis* or *C.psittaci* and so far appears to consist of only a single strain, TWAR.

*C. pneumoniae* is a common cause of community acquired pneumonia, only less frequent than *Streptococcus pneumoniae* and *Mycoplasma pneumoniae* (refs. 1, 2—Throughout this application, various references are cited in parentheses to describe more fully the state of the art to which this invention pertains. Full bibliographic information for each citation is found at the end of the specification, immediately preceding the claims. The disclosures of these references are hereby incorporated by reference into the present disclosure). *C. Pneumoniae* can also cause upper respiratory tract symptoms and disease, including bronchitis and sinusitis (refs. 1 to 4. The great majority of the adult population (over 60%) has antibodies to *C. pneumoniae* (ref. 5), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks, and recovery is slow. In approximately 10% of these cases, upper respiratory tract infection is followed by, bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections, there is no known bird or animal reservoir. Transmission has not been clearly defined. It may result from direct contact with secretions, from formites, or from airborne spread. There is a long incubation period, which may last for many months. Based on analysis of epidemics, *C. pneumoniae* appears to spread slowly through a population (case-tocase interval averaging 30 days) because infected persons are inefficient transmitters of the organism. Susceptibility to *C. pneumoniae* is universal. Reinfections occur during adulthood, following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/d, for at least 10 to 14 d). A recently developed drug, azithromycin, is highly effective as a single-dose therapy against chlamydial infections.

In most instances, *C. pneumoniae* infection is often mild and without complications, and up to 90% of infections are subacute or unrecognized. Among children in industrialized countries, infections have been thought to be rare up to the age of 5 y, although a recent study (ref. 6) has reported that many children in this age group show PCR evidence of infection despite being seronegative, and estimates a prevalence of 17 to 19% in 2 to 4 y olds. In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 y. In the USA, for example, there are estimated to be 30,000 cases of childhood pneumonia each year caused by *C. pneumoniae*. Infections may cluster among groups of children or young adults (e.g., school pupils or military conscripts).

*C. pneumoniae* causes 10 to 25% of community-acquired lower respiratory tract infections (as reported from Sweden, Italy, Finland, and the USA). During an epidemic, *C. pneumonia* infection may account for 50 to 60% of the cases of pneumonia. During these periods, also, more episodes of mixed infections with *S. pneumoniae* have been reported.

Reinfection during adulthood is common; the clinical presentation tends to be milder. Based on population seroprevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease (refs. 7 to 11). Moreover, the organisms has been detected in atheromas and fatty streaks of the coronary, carotid, peripheral arteries and aorta (refs. 12 to 16). Viable *C. pneumoniae* has been recovered from the coronary and carotid artery (refs. 17, 18). Furthermore, it has been shown that *C. pneumoniae* can induce changes of atherosclerosis in a rabbit model (ref. 19). Taken together, these results indicate that it is highly probable that *C. pneumoniae* can cause atherosclerosis in humans, though the epidemiological importance of chlamydial atherosclerosis remains to be demonstrated.

A number of recent studies have also indicated an association between *C. pneumoniae* infection and asthma. Infection has been linked to wheezing, asthmatic bronchitis, adult-onset asthma and acute exacerbations of asthma in adults, and small-scale studies have shown that prolonged antibiotic treatment was effective at greatly reducing the severity of the disease in some individuals (refs. 20 to 25).

In light of these results, a protective vaccine against *C. pneumoniae* infection would be of considerable importance. There is not yet an effective vaccine for any human chlamydial infection. Nevertheless, studies with *C. trachomatis* and *C. psittaci* indicate that this is an attainable goal. For example, mice which have recovered from a lung infection with *C. trachomitis* are protected from infertility induced by a subsequent vaginal challenge (ref. 26). Similarly, sheep immunized with inactivated *C. psittaci* were protected from subsequent chlamydial-induced abortions and stillbirths (ref. 27). Protection from chlamydial infections has been associated with Th1 immune responses, particularly the induction of INFγ-producing CD4+ T-cells (ref. 28). The adoptive transfer of CD4+ cell lines or clones to nude or SCID mice conferred protection from challenge or cleared chronic disease (refs. 29, 30), and in vivo depletion of CD4+ T cells exacerbated disease post-challenge (refs. 31, 32). However, the presence of sufficiently high titres of neutralising antibody at mucosal surfaces can also exert a protective effect (ref. 33).

The extent of antigenic variation within the species *C. pneumoniae* is not well characterised. Serovars of *C. trachomatis* are defined on the basis of antigenic variation in MOMP, but published *C. pneumoniae* MOMP gene sequences show no variation between several diverse isolates of the organism (refs. 34 to 36). The gene encoding a 76 kDa antigen has been cloned from a single strain of *C. pneumoniae* and the sequence published (ref. 48). An operon encoding the 9 kDa and 60 kDa cysteine-rich outer membrane protein genes has been described (refs. 49, 50). Many antigens recognised by immune sera to *C. pneumoniae* are conserved across all chlamydiae, but 98 kDa, 76 kDa and several other proteins may be *C. pneumoniae*-specific (refs 48, 51, 52, 53). An assessment of the number and relative frequency of any *C. pneumoniae* serotypes, and the defining antigens, is not yet possible. The entire genome sequence of *C. pneumoniae* strain CWL-029 is now known (ref. 54) and as further sequences become available a better understanding of antigenic variation may be gained.

SUMMARY OF THE INVENTION

The present invention provides purified and isolated DNA molecules that encode Chlamydia polypeptides designated inclusion membrane protein C (SEQ ID Nos: 1, 2), which can be used in methods to prevent, treat, and diagnose Chlamydia infection. The encoded polypeptides include polypeptides having the amino acid sequence shown in SEQ ID No: 3. Those skilled in the art will appreciate that the invention also includes DNA molecules that encode mutants and derivatives of such polypeptides, which result from the addition, deletion, or substitution of non-essential amino acids as described herein. The invention also includes RNA molecules corresponding to the DNA molecules of the invention.

In addition to the DNA and RNA molecules, the invention includes the corresponding polypeptides and monospecific antibodies that specifically bind to such polypeptides.

The present invention has wide application and includes expression cassettes, vectors, and cells transformed or transfected with the polynucleotides of the invention. Accordingly, the present invention provides (i) a method for producing a polypeptide of the invention in a recombinant host system and related expression cassettes, vectors, and transformed or transfected cells; (ii) a live vaccine vector, such as a pox virus, *Salmonella typhimurium*, or *Vibrio cholerae* vector, containing a polynucleotide of the invention, such vaccine vectors being useful for, e.g., preventing and treating Chlamydia infection, in combination with a diluent or carrier, and related pharmaceutical compositions and associated therapeutic and/or prophylactic methods; (iii) a therapeutic and/or prophylactic method involving administration of an RNA or DNA molecule of the invention, either in a naked form or formulated with a delivery vehicle, a polypeptide or combination of polypeptides, or a monospecific antibody of the invention, and related pharmaceutical compositions; (iv) a method for diagnosing the presence of Chlamydia in a biological sample, which can involve the use of a DNA or RNA molecule, a monospecific antibody, or a polypeptide of the invention; and (v) a method for purifying a polypeptide of the invention by antibody-based affinity chromatography.

Accordingly, in one aspect of the present invention, there is provided an isolated and purified nucleic acid molecule encoding an inclusion membrane protein C of a strain of Chlamydia or a polypeptide fragment thereof.

The isolated and purified nucleic acid molecule may have a polynucleotide sequence selected from the group consisting of:

(a) a polynucleotide sequence as set forth in FIG. 1 (SEQ ID Nos: 1, 2) or the complementary polynucleotide sequence thereto, (b) a polynucleotide sequence encoding an amino acid sequence as set forth in FIG. 1 (SEQ ID No: 3) or the complementary polynucleotide sequence thereto, (c) a polynucleotide sequence encoding a functional inclusion membrane protein C of a strain of Chlamydia, and (d) a polynucleotide sequence capable hybridizing under stringent conditions to a polynucleotide sequence (a) or (b).

BRIEF DESCRIPTION OF THE DRAWINGS

The present invention will be further understood from the following description with reference to the drawings, in which:

FIG. 1 shows the nucleotide sequence of the inclusion membrane protein C gene (SEQ ID No: 1—entire sequence and SEQ ID No: 2—coding sequence) and the deduced amino acid sequence of the inclusion membrane protein C gene from *Chlamydia pneumoniae* (SEQ ID No: 3—encoded protein);

GENERAL DESCRIPTION OF INVENTION

Figure 2E:
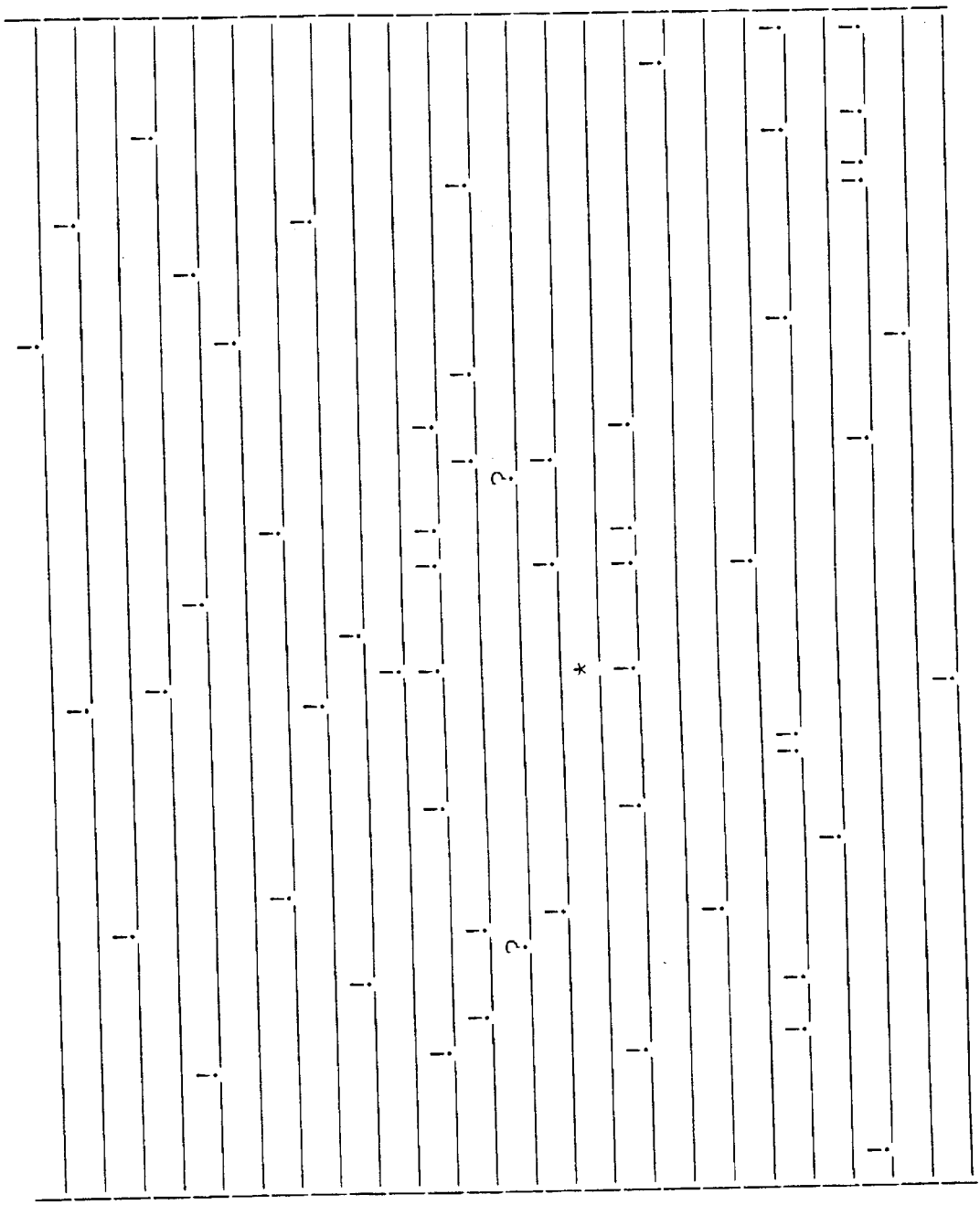
FIG. 2 shows a restriction enzyme analysis of the *C. pneumoniae* inclusion membrane protein C gene.

In the *C. pneumoniae* genome, open reading frames (ORFs) encoding chlamydial polypeptides have been identified. These polypeptides include polypeptides permanently found in the bacterial membrane structure, polypeptides that are present in the external vicinity of the bacterial membrane, include polypeptides permanently found in the inclusion membrane structure, polypeptides that are present in the external vicinity of the inclusion membrane, and potypeptides that are released into the cytoplasm of the infected cell. These polypeptides can be used in vaccination methods for preventing and treating Chlamydia infection.

According to an aspect of the invention, there are provided isolated nucleic acid molecules or polynucleotides encoding the precursor and mature forms of Chlamydia polypeptides.

An isolated polynucleotide of the invention encodes (i) a polypeptide having an amino acid sequence that is homologous to a Chlamydia amino acid sequence, the Chlamydia amino acid sequence being:

the amino acid sequence as shown in FIG. 1: (SEQ ID No: 3)

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides could be part of a vector or a composition and still be isolated in that such a vector or composition is not part of its natural environment.

A polynucleotide of the invention can be in the form of RNA or DNA (e.g., cDNA, genomic DNA, or synthetic DNA), or modifications or combinations thereof The DNA can be double-stranded or single-stranded, and, if single-stranded, can be the coding strand or the non-coding (anti-sense) strand. The sequence that encodes a polypeptide of the invention as shown in SEQ ID Nos: 1 and 2, can be (a) the coding sequence as shown in SEQ ID No: 2 (b) a ribonucleotide sequence derived by transcription of (a); or (c) a different coding sequence; this latter, as a result of the redundancy or degeneracy of the genetic code, encodes the same polypeptides as the DNA molecules of which the nucleotide sequences are illustrated in SEQ ID No: 1 or 2.

By "polypeptide" or "protein" is meant any chain of amino acids, regardless of length or post-translational modification (e.g., glycosylation or phosphorylation). Both terms are used interchangeably in the present application.

By "homologous amino acid sequence" is meant an amino acid sequence that differs from an amino acid sequence shown in SEQ ID No: 3, only by one or more conservative amino acid substitutions, or by one or more non-conservative amino acid substitutions, deletions, or additions located at positions at which they do not destroy the specific antigenicity of the polypeptide.

Preferably, such a sequence is at least 75%, more preferably 80%, and most preferably 90% identical to an amino acid sequence shown in SEQ ID No: 3.

Homologous amino acid sequences include sequences that are identical or substantially identical to an amino acid sequence as shown in SEQ ID No:3. By "amino acid sequence substantially identical" is meant a sequence that is at least 90%, preferably 95%, more preferably 97%, and most preferably 99% identical to an amino acid sequence of reference and that preferably differs from the sequence of reference, if at all, by a majority of conservative amino acid substitutions.

Conservative amino acid substitutions typically include substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Homology is typically measured using sequence analysis software (e.g., Sequence Analysis Software Package of the Genetics Computer Group, University of Wisconsin Biotechnology Center, 1710 University Avenue, Madison, Wis. 53705). Similar amino acid sequences are aligned to obtain the maximum degree of homology (i.e., identity). To this end, it may be necessary to artificially introduce gaps into the sequence. Once the optimal alignment has been set up, the degree of homology (i.e., identity) is established by recording all of the positions in which the amino acids of both sequences are identical, relative to the total number of positions.

Specifically, sequence alignments were performed using the ALIGN (Trademark) or GENALIGN (Trademark) computer programs (Inteligenetics Suite 5.4, Oxford Molecular). ALIGN® uses the Needleman-Wunsch algorithm (ref. 78) and its later modifications to locate regions of similarity between two sequences. Finding regions of maximum similarity between two sequences can be solved in a rigorous manner using the iterative matrix calculation of the Needleman and Wunsch 1997 algorithm. The analysis is restricted to regions with no internal deletions or insertions, joined by a minimum number of loop-outs or deletions. Sellers (ref.

79) developed a true metric measure of the "distance" between sequences and Waterman (ref. 80) extended this algorithm to include insertions and deletions of arbitrary length. Smith (ref. 81) improved the early algorithms to find the subsequences of maximum similarity. The algorithm has been used to analyze sequences as long as 5000 bases by dividing these sequences into segments of 200 to 400 bases, and then reassembling them into a final best match. This method of dividing the sequence and then reassembling it has proven quite robust. The algorithm permits the size of the segment to be specified which the program searches for similarities. The program then assembles the segments after checking overlaps of adjacent subsequences. The weighting of deletions and the relative size of overlaps may be controlled. The program displays the results to show the differences in closely related sequences.

GENALIGN® is a multiple alignment program. Up to 99 sequences using the Martinez/Regions (ref. 82) or Needleman-Wunsch (ref. 78) method may be analyzed for alignment. GENALIGN places the sequences in an order that puts the most closely aligned sequence pairs adjacent to each other. A consensus sequence is displayed under the multiple sequence alignments. The sequences used in developing the consensus sequence file for use in other programs. GENALIGN allows the parameters of the search to be changed so that alternate alignments of the sequences can be formed.

These programs are used employing their default settings. The default settings are as follows:

| FastDB | | |
|---|---|---|
| AMINO-Res-length | = | 2 |
| DELetion-weight | = | 5.00 |
| LEngth-factor | = | 0 |
| Matching-weight | = | 1.00 |
| NUCLEIC-Res-length | = | 4 |
| SPread-factor | = | 50 |
| Findseq | | |
| Search Parameters: | | |
| Similarity matrix | | Unitary |
| K-tuple | | 4 |
| Mismatch penalty | | 1 |
| Joining Penalty | | 30 |
| Randomization group length | | 0 |
| Cutoff score | | 5 |
| Alignment Parameters: | | |
| Window size | | 32 |
| Gap penalty | | 1.00 |
| Gap size penalty | | 0.33 |

Homologous polynucleotide sequences are defined in a similar way. Preferably, a homologous sequence is one that is at least 45%, more preferably 60%, and most preferably 85% identical to (i) a coding sequence of SEQ ID Nos:1 and 2.

Polypeptides having a sequence homologous to one of the sequences shown in SEQ ID No: 3, include naturally-occurring allelic variants, as well as mutants or any other non-naturally occurring variants that are analogous in terms of antigenicity, to a polypeptide having a sequence as shown in SEQ ID No: 3.

As is known in the art, an allelic variant is an alternate form of a polypeptide that is characterized as having a substitution, deletion, or addition of one or more amino acids that does not alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. The biological function is distinct from the antigenic function. A polypeptide can have more than one biological function.

Allelic variants are very common in nature. For example, a bacterial species, e.g., C. pneumoniae, is usually represented by a variety of strains that differ from each other by minor allelic variations. Indeed, a polypeptide that fulfills the same biological function in different strains can have an amino acid sequence that is not identical in each of the strains. Such an allelic variation may be equally reflected at the polynucleotide level.

Support for the use of allelic variants of polypeptide antigens comes from, e.g., studies of the Chlamydial MOMP antigen. The amino acid sequence of the MOMP varies from strain to strain, yet cross-strain antibody binding plus neutralization of infectivity occurs, indicating that the MOMP, when used as an immunogen, is tolerant of amino acid variations.

Polynucleotides, e.g., DNA molecules, encoding allelic variants can easily be retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers can be designed according to the nucleotide sequence information provided in SEQ ID Nos:1 and 2. Typically, a primer can consist of 10 to 40, preferably 15 to 25 nucleotides. It may be also advantageous to select primers containing C and G nucleotides in a proportion sufficient to ensure efficient hybridization; e.g., an amount of C and G nucleotides of at least 40%, preferably 50% of the total nucleotide amount.

Useful homologs that do not naturally occur can be designed using known methods for identifying regions of an antigen that are likely to be tolerant of amino acid sequence changes and/or deletions. For example, sequences of the antigen from different species can be compared to identify conserved sequences.

Polypeptide derivatives that are encoded by polynucleotides of the invention include, e.g., fragments, polypeptides having large internal deletions derived from full-length polypeptides, and fusion proteins.

Polypeptide fragments of the invention can be derived from a polypeptide having a sequence homologous to SEQ ID No: 3, to the extent that the fragments retain the substantial antigenicity of the parent polypeptide (specific antigenicity). Polypeptide derivatives can also be constructed by large internal deletions that remove a substantial part of the parent polypeptide, while retaining specific antigenicity. Generally, polypeptide derivatives should be about at least 12 amino acids in length to maintain antigenicity. Advantageously, they can be at least 20 amino acids, preferably at least 50 amino acids, more preferably at least 75 amino acids, and most preferably at least 100 amino acids in length.

Useful polypeptide derivatives, e.g., polypeptide fragments, can be designed using computer-assisted analysis of amino acid sequences in order to identify sites in protein antigens having potential as surface-exposed, antigenic regions (ref. 37).

Polypeptide fragments and polypeptides having large internal deletions can be used for revealing epitopes that are otherwise masked in the parent polypeptide and that may be of importance for inducing a protective T cell-dependent immune response. Deletions can also remove immunodominant regions of high variability among strains.

It is an accepted practice in the field of immunology to use fragments and variants of protein immunogens as vaccines, as all that is required to induce an immune response to a protein is a small (e.g., 8 to 10 amino acid) immunogenic region of the protein. This has been done for a number of vaccines against pathogens other than Chlamydia. For example, short synthetic peptides corresponding to surface-exposed antigens of pathogens such as murine mammary tumor virus, peptide containing 11 amino acids; (ref. 38), Semliki Forest virus, peptide containing 16 amino acids (ref. 39), and canine parvovirus, 2 overlapping peptides, each containing 15 amino acids (ref. 40), have been shown to be effective vaccine antigens against their respective pathogens.

Polynucleotides encoding polypeptide fragments and polypeptides having large internal deletions can be constructed using standard methods (ref. 41), for example, by PCR, including inverse PCR, by restriction enzyme treatment of the cloned DNA molecules, or by the method of Kunkel et al. (ref. 42) biological material available at Stratagene.

A polypeptide derivative can also be produced as a fusion polypeptide that contains a polypeptide or a polypeptide derivative of the invention fused, e.g., at the N- or C-terminal end, to any other polypeptide (hereinafter referred to as a peptide tail). Such a product can be easily obtained by translation of a genetic fusion, i.e., a hybrid gene. Vectors for expressing fusion polypeptides are commercially available, such as the pMal-c2 or pMal-p2 systems of New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

Another particular example of fusion polypeptides included in invention includes a polypeptide or polypeptide derivative of the invention fused to a polypeptide having adjuvant activity, such as, e.g., subunit B of either cholera toxin or *E. coli* heat-labile toxin. Several possibilities are can be used for achieving fusion. First, the polypeptide of the invention can be fused to the N-, or preferably, to the C-terminal end of the polypeptide having adjuvant activity. Second, a polypeptide fragment of the invention can be fused within the amino acid sequence of the polypeptide having adjuvant activity.

As stated above, the polynucleotides of the invention encode Chlamydia polypeptides in precursor or mature form. They can also encode hybrid precursors containing heterologous signal peptides, which can mature into polypeptides of the invention. By "heterologous signal peptide" is meant a signal peptide that is not found in the naturally-occurring precursor of a polypeptide of the invention.

A polynucleotide of the invention, having a homologous coding sequence, hybridizes, preferably under stringent conditions, to a polynucleotide having a sequence as shown in SEQ ID Nos:1 to 2. Hybridization procedures are, e.g., described in Ausubel et al., (ref. 41), Silhavy et al. (ref. 43); Davis et al. (ref. 44). Important parameters that can be considered for optimizing hybridization conditions are reflected in a formula that allows calculation of a critical value, the melting temperature above which two complementary DNA strands separate from each other ref. 45). This formula is as follows: Tm=81.5+0.41×(% G+C)+16.6 log (cation ion concentration)−0.63×(% formamide)−600/base number. Under appropriate stringency conditions, hybridization temperature (Th) is approximately 20 to 40° C., 20 to 25° C., or, preferably 30 to 40° C. below the calculated Tm. Those skilled in the art will understand that optimal temperature and salt conditions can be readily determined empirically in preliminary experiments using conventional procedures.

For example, stringent conditions can be achieved, both for pre-hybridizing and hybridizing incubations, (i) within 4 to 16 hours at 42° C., in 6×SSC containing 50% formamide or (ii) within 4–16 hours at 65° C. in an aqueous 6×SSC solution (1 M NaCl, 0.1 M sodium citrate (pH 7.0)). Typically, hybridization experiments are performed at a temperature from 60 to 68° C., e.g. 65° C. At such a temperature, stringent hybridization conditions can be achieved in 6×SSC, preferably in 2×SSC or 1×SSC, more preferably in 0.5×SSc, 0.3×SSC or 0.1×SSC (in the absence of formamide). 1×SSC contains 0.15 M NaCl and 0.015 M sodium citrate.

For polynucleotides containing 30 to 600 nucleotides, the above formula is used and then is corrected by subtracting (600/polynucleotide size in base pairs). Stringency conditions are defined by a Th that is 5 to 10° C. below Tm.

Hybridization conditions with oligonucleotides shorter than 20 to 30 bases do not exactly follow the rules set forth above. In such cases, the formula for calculating the Tm is as follows: Tm=4×(G+C)+2 (A+T). For example, an 18 nucleotide fragment of 50% G+C would have an approximate Tm of 54° C.

A polynucleotide molecule of the invention, containing RNA, DNA, or modifications or combinations thereof, can have various applications. For example, a DNA molecule can be used (i) in a process for producing the encoded polypeptide in a recombinant host system, (ii) in the construction of vaccine vectors such as poxviruses, which are further used in methods and compositions for preventing and/or treating Chlamydia infection, (iii) as a vaccine agent (as well as an RNA molecule), in a naked form or formulated with a delivery vehicle and, (iv) in the construction of attenuated Chlamydia strains that can over-express a polynucleotide of the invention or express it in a non-toxic, mutated form.

According to further aspects of the invention, there are provided (i) an expression cassette containing a DNA molecule of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system can be selected from procaryotic and eucaryotic hosts. Eucaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. Preferably, a procaryotic host such as *E coli* is used. Bacterial and eucaryotic cells are available from a number of different sources to those skilled in the art, e.g., the American Type Culture Collection (ATCC; 10801 University Blvd., Manassas, Va. 20110-2209, USA).

The choice of the expression system depends on the features desired for the expressed polypeptide. For example, it may be useful to produce a polypeptide of the invention in a particular lipidated form or any other form.

The choice of the expression cassette will depend on the host system selected as well as the features desired for the expressed polypeptide. Typically, an expression cassette includes a promoter that is functional in the selected host system and can be constitutive or inducible; a ribosome binding site; a start codon (ATG) if necessary, a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region can be homologous or heterologous to the DNA molecule encoding the mature polypeptide and can be specific to the secretion apparatus of the host used for expression. The open reading frame constituted by the DNA molecule of the invention, solely or together with the signal peptide, is placed under the control of the promoter so that transcription and translation occur in the host system. Promoters, signal peptide encoding regions are widely known and available to those skilled in the art and includes, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., (ref. 46); the promoter of the gene of bacteriophage T7 encoding RNA polymerase, that is functional in a number of *E. coli* strains expressing T7 polymerase (described in U.S. Pat. No. 4,952, 496); OspA lipidation signal peptide; and RIpB lipidation signal peptide (ref. 47).

The expression cassette is typically part of an expression vector, which is selected for its ability to replicate in the chosen expression system. Expression vectors (e.g., plasmids or viral vectors) can be chosen from those described in Pouwels et al. (Cloning Vectors: A Laboratory Manual 1985, Supp. 1987). They can be purchased from various commercial sources.

Methods for transforming/transfecting host cells with expression vectors will depend on the host system selected as described in Ausubel et al., (ref. 41).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide can then be recovered in a substantially purified form from the cell extract or from the supernatant after centrifugation of the recombinant cell culture. Typically, the recombinant polypeptide can be purified by antibody-based affinity purification or by any other method that can be readily adapted by a person skilled in the art, such as by genetic fusion to a small affinity binding domain. Antibody-based affinity purification methods are also available for purifying a polypeptide of the invention extracted from a Chlamydia strain. Antibodies useful for purifying by immunoaffinity the polypeptides of the invention can be obtained as described below.

A polynucleotide of the invention can also be useful in the vaccine field, e.g., for achieving DNA vaccination. There are two major possibilities, either using a viral or bacterial host as gene delivery vehicle (live vaccine vector) or administering the gene in a free form, e.g., inserted into a plasmid. Therapeutic or prophylactic efficacy of a polynucleotide of the invention can be evaluated as described below.

Accordingly, in additional aspects of the invention, there are provided (i) a vaccine vector such as a poxvirus, containing a DNA molecule of the invention, placed under the control of elements required for expression; (ii) a composition of matter containing a vaccine vector of the invention, together with a diluent or carrier; particularly, (iii) a pharmaceutical composition containing a therapeutically or prophylactically effective amount of a vaccine vector of the invention; (iv) a method for inducing an immune response against Chlamydia in a mammal (e.g., a human; alternatively, the method can be used in veterinary applications for treating or preventing Chlamydia infection of animals, e.g., cats or birds), which involves administering to the mammal an immunogenically effective amount of a vaccine vector of the invention to elicit an immune response, e.g., a protective or therapeutic immune response to Chlamydia ; and particularly, (v) a method for preventing and/or treating a Chlamydia (e.g., *C. trachomitis, C. psittaci, C. pneumonia, C. pecorum*) infection, which involves administering a prophylactic or therapeutic amount of a vaccine vector of the invention to an individual in need. Additionally, the invention encompasses the use of a vaccine vector of the invention in the preparation of a medicament for preventing and/or treating Chlamydia infection.

Figure 3:
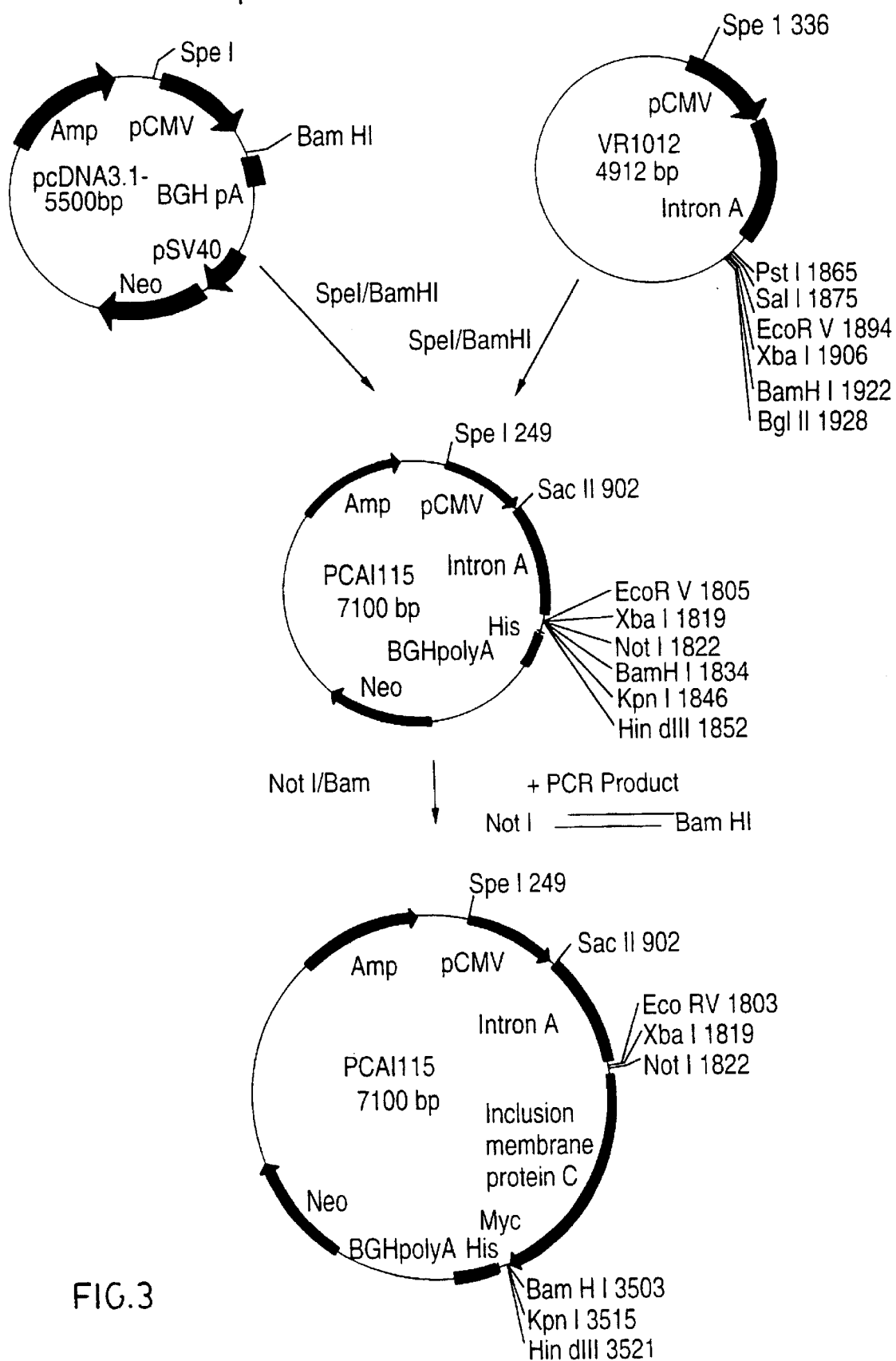
FIG. 3 shows a scheme of the construction and elements of plasmid pCAI115.

The vaccine vector may be a plasmid vector incapable of separation in mammalian cells. The elements for expression may include a promoter suitable for expression in mammalian cells, particularly a cytomegalovirus vector. The plasmid vector particularly has the identifying characteristics of plasmid pCAI115 as shown in FIG. 3.

A vaccine vector of the invention can express one or several polypeptides or derivatives of the invention, as well as at least one additional Chlamydia antigen, fragment, homolog, mutant, or derivative thereof. In addition, it can express a cytokine, such as interleukin-2 (IL-2) or interleukin-12 (IL-12), that enhances the immune response (adjuvant effect). Thus, a vaccine vector can include an additional DNA sequence encoding, e.g., a chlamydial antgen, or a cytokine, placed under the control of elements required for expression in a mammalian cell.

Alternatively, a composition of the invention can include several vaccine vectors, each of them being capable of expressing a polypeptide or derivative of the invention. A composition can also contain a vaccine vector capable of expressing an additional Chlamydia antigen, or a subunit, fragment, homolog, mutant, or derivative thereof; or a cytokine such as IL-2 or IL-12.

In vaccination methods for treating or preventing infection in a mammal, including a human host, a vaccine vector of the invention can be administered by any conventional route in use in the vaccine field, particularly, to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. The administration can be achieved in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses and poxviruses as well as bacterial vectors, e.g., Shigella, Salmonella, *Vibrio cholerae*, Lactobacillus, Bacille bilié de Calmette-Guérin (BCG), and Streptococcus.

An example of an adenovirus vector, as well as a method for constructing an adenovirus vector capable of expressing a DNA molecule of the invention, are described in U.S. Pat. No. 4,920,209. Poxvirus vectors that can be used include, e.g., vaccinia and canary pox virus, described in U.S. Pat. No. 4,722,848 and U.S. Pat. No. 5,364,773, respectively (also see, e.g., ref. 54A for a description of a vaccinia virus vector; and ref. 55 for a reference of a canary pox). Poxvirus vectors capable of expressing a polynucleotide of the invention can be obtained by homologous recombination as described in ref. 56 so that the polynucleotide of the invention is inserted in the viral genome under appropriate conditions for expression in mammalian cells. Generally, the dose of vaccine viral vector, for therapeutic or prophylactic use, can be of from about $1 \times 10^4$ to about $1 \times 10^{11}$, advantageously from about $1 \times 10^7$ to about $1 \times 10^{10}$, preferably of from about $1 \times 10^7$ to about $1 \times 10^9$ plaque-forming units per kilogram. Preferably, viral vectors are administered parenterally; for example, in 3 doses, 4 weeks apart. Those skilled in the art recognize that it is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are described in ref. 57 and U.S. Pat. No. 4,882,278 (strain in which a substantial amount of the coding sequence of each of the two ctxA alleles has been deleted so that no functional cholerae toxin is produced); WO 92/11354 (strain in which the irgA locus is inactivated by mutation; this mutation can be combined in a single strain with ctxA mutations); and WO 94/1533 (deletion mutant lacking functional ctxa and attRS1 DNA sequences). These strains can be genetically engineered to express heterologous antigens, as described in WO 94/19482. An effective vaccine dose of a *Vibrio cholerae* strain capable of expressing a polypeptide or polypeptide derivative encoded by a DNA molecule of the invention can contain, e.g., about $1 \times 10^5$ to about $1 \times 10^9$, preferably about $1 \times 10^6$ to about $1 \times 10^8$ viable bacteria in an appropriate volume for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in ref. 58 and WO 92/11361. Preferred routes of administration include all mucosal routes; most preferably, these vectors are administered intranasally or orally.

Others bacterial strains useful as vaccine vectors are described in refs. 59, 60 (*Shigella flexnen*); ref. 61 (*Streptococcus gordonii*); and ref. 62, WO 88/6626, WO 90/0594, WO 91/13157, WO 92/1796, and WO 92/21376 (*Bacille Calmette Guerin*).

In bacterial vectors, polynucleotide of the invention can be inserted into the bacterial genome or can remain in a free state, carried on a plasmid.

An adjuvant can also be added to a composition containing a vaccine bacterial vector. A number of adjuvants are known to those skilled in the art. Preferred adjuvants can be selected from the list provided below.

According to additional aspects of the invention, there are also provided (i) a composition of matter containing a polynucleotide of the invention, together with a diluent or carrier, (ii) a pharmaceutical composition containing a therapeutically or prophylactically effective amount of a polynucleotide of the invention; (iii) a method for inducing an immune response against Chlamydia, in a mammal, by administering to the mammal, an immunogenically effective amount of a polynucleotide of the invention to elicit an immune response, e.g., a protective immune response to Chlamydia; and particularly, (iv) a method for preventing and/or treating a Chlamydia (e.g., *C. trachomitis, C. psittaci, C. pneumoniae*, or *C. pecorum*) infection, by administering a prophylactic or therapeutic amount of a polynucleotide of the invention to an individual in need. Additionally, the invention encompasses the use of a polynucleotide of the invention in the preparation of a medicament for preventing and/or treating Chlamydia infection. The invention preferably includes the use of a DNA molecule placed under conditions for expression in a mammalian cell, e.g., in a plasmid that is unable to replicate in mammalian cells and to substantially integrate in a mammalian genome.

Polynucleotides (DNA or RNA) of the invention can also be administered as such to a mammal for vaccine, e.g., therapeutic or prophylactic, purpose. When a DNA molecule of the invention is used, it can be in the form of a plasmid that is unable to replicate in a mammalian cell and unable to integrate in the mammalian genome. Typically, a DNA molecule is placed under the control of a promoter suitable for expression in a mammalian cell. The promoter can function ubiquitously or tissue-specifically. Examples of non-tissue specific promoters include the early Cytomegalovirus (CMV) promoter (described in U.S. Pat. No. 4,168,062) and the Rous Sarcoma Virus promoter (described in ref. 63). The desmin promoter (refs. 64, 65, 66) is tissue-specific and drives expression in muscle cells. More generally, useful vectors are described, ia., WO 94/21797 and ref. 67.

For DNA/RNA vaccination, the polynucleotide of the invention can encode a precursor or a mature form. When it encodes a precursor form, the precursor form can be homologous or heterologous. In the latter case, a eucaryotic leader sequence can be used, such as the leader sequence of the tissue-type plasminogen factor (tPA).

A composition of the invention can contain one or several polynucleotides of the invention. It can also contain at least one additional polynucleotide encoding another Chlamydia antigen, such as urease subunit A, B, or both; or a fragment, derivative, mutant, or analog thereof. A polynucleotide encoding a cytokine, such as interieukin-2 (IL-2) or interleukin-12 (IL-12), can also be added to the composition so that the immune response is enhanced. These additional polynucleotides are placed under appropriate control for expression. Advantageously, DNA molecules of the invention and/or additional DNA molecules to be included in the same composition, can be carried in the same plasmid.

Standard techniques of molecular biology for preparing and purifying polynucleotides can be used in the preparation of polynucleotide therapeutics of the invention. For use as a vaccine, a polynucleotide of the invention can be formulated according to various methods.

First, a polynucleotide can be used in a naked form, free of any delivery vehicles, such as anionic liposomes, cationic lipids, microparticles, e.g., gold microparticles, precipitating agents, e.g., calcium phosphate, or any other transfection-faciliating agent. In this case, the polynucleotide can be simply diluted in a physiologically acceptable solution, such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

Alternatively, a polynucleotide can be associated with agents that assist in cellular uptake. It can be, ia., (i) complemented with a chemical agent that modifies the cellular permeability, such as bupivacaine (see, e.g., WO 94/16737), (ii) encapsulated into liposomes, or (iii) associated with cationic lipids or silica, gold, or tungsten microparticles.

Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy)propyl]-N,N,N-trimethylammonium chloride), DOTAP (1,2-bis(oleyloxy)3-(trimethylammonio)propane), DDAB (dimethyldioctadecylammonium bromide), DOGS (dioctadecylamidologlycyl spermine) and cholesterol derivatives such as DC-Chol (3 beta-(N-(N',N'-dimethyl aminomethane)-carbamoyl)cholesterol). A description of these cationic lipids can be found in EP 187,702, WO 90111092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as, for example, described in WO 90/11092.

Other transfection-facilitating compounds can be added to a formulation containing cationic liposomes. A number of them are described in, e.g., WO 93/18759, WO 93119768, WO 94/25608, and WO 9512397. They include, i.a., spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles can also be used for gene delivery, as described in WO 91/359, WO 93/17706, and ref. 68. In this case, the microparticle-coated polynucleotides can be injected via intradermal or intraepidermal routes using a needleless injection device ("gene gun"), such as those described in ref. 69 and in U.S. Pat. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 $\mu$g to about 1 mg, preferably, from about 10 $\mu$g to about 800 $\mu$g and, more preferably, from about 25 $\mu$g to about 250 $\mu$g, can be administered to human adults. The administration can be achieved in a single dose or repeated at intervals.

The route of administration can be any conventional route used in the vaccine field. As general guidance, a polynucleotide of the invention can be administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of the administration route will depend on, e.g., the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or subcutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that can be useful in diagnosis. Accordingly, in a further aspect of the invention, there is provided a nucleotide probe or primer having a sequence found in or derived by degeneracy of the genetic code from a sequence shown in SEQ ID Nos: 1 to 2.

The term "probe" as used in the present application refers to DNA (preferably single stranded) or RNA molecules (or modifications or combinations thereof) that hybridize under the stringent conditions, as defined above, to nucleic acid molecules having sequences homologous to those shown in SEQ ID Nos: 1 and 2, or to a complementary or anti-sense sequence. Generally, probes are significantly shorter than full-length sequences shown in SEQ ID Nos: 1 and 2; for example, they can contain from about 5 to about 100, preferably from about 10 to about 80 nucleotides. In particular, probes have sequences that are at least 75%, preferably at least 85%, more preferably 95% homologous to a portion of a sequence as shown in SEQ ID Nos: 1 and 2 or that are complementary to such sequences. Probes can contain modified bases such as inosine, methyl-5-deoxycytidine, deoxyuridine, dimethylamino-5-deoxyuridine, or diamino-2,6-purine. Sugar or phosphate residues can also be modified or substituted. For example, a deoxyribose residue can be replaced by a polyamide (ref. 70) and phosphate residues can be replaced by ester groups such as diphosphate, alkyl, arylphosphonate and phosphorothioate esters. In addition, the 2'-hydroxyl group on ribonucleotides can be modified by including, e.g., alkyl groups.

Probes of the invention can be used in diagnostic tests, as capture or detection probes. Such capture probes can be conventionally immobilized on a solid support, directly or indirectly, by covalent means or by passive adsorption. A detection probe can be labelled by a detection marker selected from radioactive isotopes; enzymes such as peroxidase, alkaline phosphatase, and enzymes able to hydrolyze a chromogenic, fluorogenic, or luminescent substrate; compounds that are chromogenic, fluorogenic, or luminescent; nucleotide base analogs; and biotin.

Probes of the invention can be used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot (ref. 71), northern blot (identical to Southern blot to the exception that RNA is used as a target), or the sandwich technique (ref. 72). The latter technique involves the use of a specific capture probe and/or a specific detection probe with nucleotide sequences that at least partially differ from each other.

A primer is usually a probe of about 10 to about 40 nucleotides that is used to initiate enzymatic polymerization of DNA in an amplification process (e.g., PCR), in an elongation process, or in a reverse transcription method. In a diagnostic method involving PCR, primers can be labelled.

Thus, the invention also encompasses (i) a reagent containing a probe of the invention for detecting and/or identifying the presence of Chlamydia in a biological material;

(ii) a method for detecting and/or identifying the presence of Chlamydia in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of Chlamydia in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

As previously mentioned, polypeptides that can be produced upon expression of the newly identified open reading frames are useful vaccine agents.

Therefore, an additional aspect of the invention features a substantially purified polypeptide or polypeptide derivative having an amino acid sequence encoded by a polynucleotide of the invention.

A "substantially purified polypeptide" is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art will understand that the polypeptides of the invention can be purified from a natural source, i.e., a Chlamydia strain, or can be produced by recombinant means.

Homologous polypeptides or polypeptide derivatives encoded by polynucleotides of the invention can be screened for specific antigenicity by testing cross-reactivity with an antiserum raised against the polypeptide of reference having an amino acid sequence as shown in SEQ ID No:3. Briefly, a monospecific hyperimmune antiserum can be raised against a purified reference polypeptide as such or as a fusion polypeptide, for example, an expression product of MBP, GST, or His-tag systems or a synthetic peptide predicted to be antigenic. The homologous polypeptide or derivative screened for specific antigenicity can be produced as such or as a fusion polypeptide. In this latter case and if the antiserum is also raised against a fusion polypeptide, two different fusion systems are employed. Specific antigenicity can be determined according to a number of methods, including Western blot (ref. 73), dot blot, and ELISA, as described below.

In a Western blot assay, the product to be screened, either as a purified preparation or a total $E.\ coli$ extract, is submitted to SDS-Page electrophoresis as described by Laemmli (ref. 74). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 $\mu$l of a preparation at about 10 $\mu$g protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 $\mu$l PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 $\mu$l of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 $\mu$g/ml is serially two-fold diluted in 50 mM Tris-HCl (pH 7.5). 100 $\mu$l of each dilution are applied to a nitrocellulose membrane 0.45 $\mu$m set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below.

According to additional aspects of the invention, there are provided (i) a composition of matter containing a polypeptide of the invention together with a diluent or carrier; in particular, (ii) a pharmaceutical composition containing a therapeutically or prophylactically effective amount of a polypeptide of the invention; (iii) a method for inducing an immune response against Chlamydia in a mammal, by administering to the mammal an immunogenically effective amount of a polypeptide of the invention to elicit an immune response, e.g., a protective immune response to Chlamydia; and particularly, (iv) a method for preventing and/or treating a Chlamydia (e.g., *C. trachomitis. C. psittaci, C. pneumoniae* or *C. pecorum*) infection, by administering a prophylactic or therapeutic amount of a polypeptide of the invention to an individual in need. Additionally, the seventh aspect of the invention encompasses the use of a polypeptide of the invention in the preparation of a medicament for preventing and/or treating Chlamydia infection.

The immunogenic compositions of the invention can be administered by any conventional route in use in the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of the administration route depends upon a number of parameters, such as the adjuvant associated with the polypeptide. For example, if a mucosal adjuvant is used, the intranasal or oral route will be preferred and if a lipid formulation or an aluminum compound is used, the parenteral route will be preferred. In the latter case, the sub-cutaneous or intramuscular route is most preferred. The choice can also depend upon the nature of the vaccine agent. For example, a polypeptide of the invention fused to CTB or LTB will be best administered to a mucosal surface.

A composition of the invention can contain one or several polypeptides or derivatives of the invention. It can also contain at least one additional Chlamydia antigen, or a subunit, fragment, homolog, mutant, or derivative thereof.

For use in a composition of the invention, a polypeptide or derivative thereof can be formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see Liposomes: A Practical Approach (supra).

Adjuvants other than liposomes and the like can also be used and are known in the art. A appropriate selection can conventionally be made by those skilled in the art, for example, from the list provided below.

Administration can be achieved in a single dose or repeated as necessary at intervals as can be determined by one skilled in the art. For example, a priming dose can be followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention can be administered by a mucosal route in an amount from about 10 $\mu$g to about 500 mg, preferably from about 1 mg to about 200 mg. For the parenteral route of administration, the dose usually should not exceed about 1 mg, preferably about 100 $\mu$g.

When used as vaccine agents, polynucleotides and polypeptides of the invention can be used sequentially as part of a multistep immunization process. For example, a mammal can be initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention can also be used for priming, with boosting being carried out mucosally using a soluble polypeptide or derivative of the invention in combination with a mucosal adjuvant (e.g., LT).

A polypeptide derivative of the invention is also useful as a diagnostic reagent for detecting the presence of anti-Chlamydia antibodies, e.g., in a blood sample. Such polypeptides are about 5 to about 80, preferably about 10 to about 50 amino acids in length and can be labeled or unlabeled, depending upon the diagnostic method. Diagnostic methods involving such a reagent are described below.

Upon expression of a DNA molecule of the invention, a polypeptide or polypeptide derivative is produced and can be purified using known laboratory techniques. For example, the polypeptide or polypeptide derivative can be produced as a fusion protein containing a fused tail that facilitates purification. The fusion product can be used to immunize a small mammal, e.g., a mouse or a rabbit, in order to raise antibodies against the polypeptide or polypeptide derivative (monospecific antibodies). The eighth aspect of the invention thus provides a monospecific antibody that binds to a polypeptide or polypeptide derivative of the invention.

By "monospecific antibody" is meant an antibody that is capable of reacting with a unique naturally-occurring Chlamydia polypeptide. An antibody of the invention can be polyclonal or monoclonal. Monospecific antibodies can be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies can also be in the form of immunoglobulin fragments, e.g., F(ab)'2 or Fab fragments. The antibodies of the invention can be of any isotype, e.g., IgG or IgA, and polyclonal antibodies can be of a single isotype or can contain a mixture of isotypes.

The antibodies of the invention, which are raised to a polypeptide or polypeptide derivative of the invention, can be produced and identified using standard immunological assays, e.g., Western blot analysis, dot blot assay, or ELISA (see, e.g., Coligan et al., Current Protocols in Immunology (1994) John Wiley & Sons, Inc., New York, N.Y.). The antibodies can be used in diagnostic methods to detect the presence of a Chlamydia antigen in a sample, such as a biological sample. The antibodies can also be used in affinity chromatography methods for purifying a polypeptide or polypeptide derivative of the invention. As is discussed further below, such antibodies can be used in prophylactic and therapeutic passive immunization methods.

Accordingly, further aspects of the invention provides (i) a reagent for detecting the presence of Chlamydia in a biological sample that contains an antibody, polypeptide, or polypeptide derivative of the invention; and (ii) a diagnostic method for detecting the presence of Chlamydia in a biological sample, by contacting the biological sample with an antibody, a polypeptide, or a polypeptide derivative of the invention, such that an immune complex is formed, and by detecting such complex to indicate the presence of Chlamydia in the sample or the organism from which the sample is derived.

Those skilled in the art will understand that the immune complex is formed between a component of the sample and the antibody, polypeptide, or polypeptide derivative, whichever is used, and that any unbound material can be removed prior to detecting the complex. As can be easily understood, a polypeptide reagent is useful for detecting the presence of anti-Chlamydia antibodies in a sample, e.g., a blood sample, while an antibody of the invention can be used for screening a sample, such as a gastric extract or biopsy, for the presence of Chlamydia polypeptides.

For use in diagnostic applications, the reagent (i.e., the antibody, polypeptide, or polypeptide derivative of the invention) can be in a free state or immobilized on a solid support, such as a tube, a bead, or any other conventional support used in the field. Immobilization can be achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means can also employ a ligand-receptor system, for example, a molecule such as a vitamin can be grafted onto the polypeptide reagent and the corresponding receptor can be immobilized on the solid phase. This is illustrated by the biotin-streptavidin system. Alternatively, indirect means can be used, e.g., by adding to the reagent a peptide tail, chemically or by genetic engineering, and immobilizing the grafted or fused product by passive adsorption or covalent linkage of the peptide tail.

According to a further aspect of the invention, there is provided a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody can be polyclonal or monospecific, and preferably is of the IgG type. Purified IgGs can be prepared from an antiserum using standard methods (see, e.g., Coligan et al., supra). Conventional chromatography supports, as well as standard methods for grafting antibodies, are disclosed in, e.g., Antibodies: A Laboratory Manual, D. Lane, E. Harlow, Eds. (1988).

Briefly, a biological sample, such as an C. pneumoniae extract, preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, can be in batch form or in a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

An antibody of the invention can be screened for therapeutic efficacy as described as follows. According to additional aspects of the invention, there are provided (i) a composition of matter containing a monospecific antibody of the invention, together with a diluent or carrier; (ii) a pharmaceutical composition containing a therapeutically or prophylactically effective amount of a monospecific antibody of the invention, and (iii) a method for treating or preventing a Chlamydia (e.g., C. trachomitis, C. psittaci, C. pneumoniae or C. pecorum) infection, by administering a therapeutic or prophylactic amount of a monospecific antibody of the invention to an individual in need. Additionally, an additional aspect of the invention encompasses the use of a monospecific antibody of the invention in the preparation of a medicament for treating or preventing Chlamydia infection.

To this end, the monospecific antibody can be polyclonal or monoclonal, preferably of the IgA isotype (predominantly). In passive immunization, the antibody can be administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, can be carried out. A monospecific antibody of the invention can be administered as a single active component or as a mixture with at least one monospecific antibody specific for a different Chlamydia polypeptide. The amount of antibody and the particular regimen used can be readily determined by one skilled in the art. For example, daily administration of about 100 to 1,000 mg of antibodies over one week, or three doses per day of about 100 to 1,000 mg of antibodies over two or three days, can be an effective regimens for most purposes.

Therapeutic or prophylactic efficacy can be evaluated using standard methods in the art, e.g., by measuring induction of a mucosal immune response or induction of protective and/or therapeutic immunity, using, e.g., the C. pneumoniae mouse model. Those skilled in the art will recognize that the C. pneumoniae strain of the model can be replaced with another Chlamydia strain. For example, the efficacy of DNA molecules and polypeptides from C. pneumoniae is preferably evaluated in a mouse model using an C. pneumoniae strain. Protection can be determined by comparing the degree of Chlamydia infection to that of a control group. Protection is shown when infection is reduced by comparison to the control group. Such an evaluation can be made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen can be precipitated with, or adsorbed onto, the aluminum compound according to standard protocols. Other adjuvants, such as RIBI (ImmunoChem, Hamilton, Mont.), can be used in parenteral administration.

Adjuvants for mucosal administration include bacterial toxins, e.g., the cholera toxin (CT), the E. coli heat-labile toxin (LT), the Clostridium difficile toxin A and the pertussis toxin (PT), or combinations, subunits, toxoids, or mutants thereof. For example, a purified preparation of native cholera toxin subunit B (CTB) can be of use. Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that can be used in the methods and compositions of the invention include, e.g., Ser-63-Lys, Ala-69-Gly, Glu-110Asp, and Glu-112-Asp mutants. Other adjuvants, such as a bacterial monophosphoryl lipid A (MPLA) of, e.g., E coli, Salmonella minnesota, Salmonella typhimurium, or Shigella flexneri; saponins, or polylactide glycolide (PLGA) microspheres, can also be used in mucosal administration.

Adjuvants useful for both mucosal and parenteral administrations include polyphosphazene (WO 9512415), DC-chol (3 b-(N-(N',N'-dimethylaminomethane)-carbamoyl)cholesterol; U.S. Pat. No. 5,283,185 and WO 96/14831) and QS-21 (WO 88/9336).

Any pharmaceutical composition of the invention, containing a polynucleotide, a polypeptide, a polypeptide derivative, or an antibody of the invention, can be manufactured in a conventional manner. In particular, it can be formulated with a pharmaceutically acceptable diluent or carrier, e.g., water or a saline solution such as phosphate buffer saline. In general, a diluent or carrier can be selected on the basis of the mode and route of administration, and standard pharmaceutical practice. Suitable pharmaceutical carriers or diluents, as well as pharmaceutical necessities for their use in pharmaceutical formulations, are described in Remington's Pharmaceutical Sciences, a standard reference text in this field and in the USP/NF.

The invention also includes methods in which Chlamydia infection, are treated by oral administration of a Chlamydia polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids. In addition, compounds containing more than one of the above-listed components coupled together, can be used. The invention also includes compositions for carrying out these methods, ie., compositions containing a Chlamydia antigen (or antigens) of the invention, an adjuvant, and one or more of the above-listed compounds, in a pharmaceutically acceptable carrier or diluent.

It has recently been shown that the 60 kDa cysteine rich membrane protein contains a sequence cross-reactive with the murine alpha-myosin heavy chain epitope M7A-alpha, an epitope conserved in humans (ref. 75). This cross-reactivity is proposed to contribute to the development of cardiovascular disease, so it may be beneficial to remove this epitope, and any other epitopes cross-reactive with human antigens, from the protein if it is to be used as a vaccine. This could be achieved by modification of the coding sequence, for example, deletion or substitution of the nucleotides encoding the epitope from polynucleotides encoding the protein. A similar approach may be appropriate for any protective antigen found to have unwanted homologies or cross-reactivities with human antigens.

Amounts of the above-listed compounds used in the methods and compositions of the invention can readily be determined by one skilled in the art. In addition, one skilled in the art can readily design treatment/immunization schedules. For example, the non-vaccine components can be administered on days 1–14, and the vaccine antigen+adjuvant can be administered on days 7,14, 21, and 28.

EXAMPLES

The above disclosure generally discribes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This Example illustrates the preparation of a plasmid vector pCAI115 containing the inclusion membrane protein C gene.

The inclusion membrane protein C gene was amplified from *Chlamydia pneumoniae* strain CMI genomic DNA by polymerase chain reaction (PCR) using a 5' primer (5' ATAAGAAT GCGGCCGCCACCATGACCTCACCGATCCCCTTTCAG 3') (SEQ ID No: 4) and a 3' primer (5' GCGCC GGATCCGAGAAGCCGGTAGAGGCGTG 3') (SEQ ID No: 5). The 5' primer contains a NotI restriction site, a ribosome binding site, an initiation codon and a sequence at the 5' end of the inclusion membrane protein C coding sequence (SEQ ID No: 2). The 3' primer includes the sequence encoding the C-terminal sequence of the inclusion membrane protein C and a BamHI restriction site. The stop codon was excluded and an additional nucleotide was inserted to obtain an in-frame fusion with the Histidine tag.

After amplification of the genomic DNA, the PCR fragment was purified using QIAquick™ PCR purification kit (Qiagen) and then digested with NotI and BamHI and cloned into the pCA-Myc-His eukaryotic expression vector described in Example 2 (FIG. 3) with transcription under control of the human CMV promoter.

Example 2

This Example illustrates the preparation of the eukaryotic expression vector pCAI115.

Plasmid pcDNA3.1(−)Myc-His C (Invitrogen) was restricted with SpeI and BamHI to remove the CMV promoter and the remaining vector fragment was isolated. The CMV promoter and intron A from plasmid VR-1012 (Vical) was isolated on a SpeI/BamHI fragment. The fragments were ligated together to produce plasmid pCA/Myc-His. The NotI/BamHI restricted PCR fragment containing the inclusion membrane protein C gene from Example 1 was ligated into the NotI and BamHI restricted plasmid pCA/Myc-His to produce plasmid pCAI 115 (FIG. 3).

The resulting plasmid, pCAI115, was transfered by electroporation into *E. coli* XL-1 blue (Stratagene) which was grown in LB broth containing 50 μg/ml of carbenicillin. The plasmid was isolated by Endo Free Plasmid Giga Kit™ (Qiagen) large scale DNA purification system. DNA concentration was determined by absorbance at 260 nm and the plasmid was verified after gel electrophoresis and Ethidium bromide staining and comparison to molecular weight standards. The 5' and 3' ends of the gene were verified by sequencing using a LiCor model 4000 L DNA sequencer and IRD-800 labelled primers.

Example 3

This Example illustrates the immunization of mice to achieve protection against an intranasal challenge by *C. pneumoniae.*

It has been previously demonstrated (ref. 76) that mice are susceptible to intranasal infection with different isolates of *C. pneumoniae*. Strain AR-39 (ref. 77) was used in Balbic mice as a challenge infection model to examine the capacity of chlamydia gene products delivered as naked DNA to elicit a protective response against a sublethal *C. pneumoniae* lung infection. Protective immunity is defined as an accelerated clearance of pulmonary infection.

Groups of 7 to 9 week old male Balb/c mice (8 to 10 per group) were immunized intramuscularly (i.m.) plus intranasally (i.n.) with plasmid DNA containing the coding sequence of *C. pneumoniae* inclusion membrane protein C, prepared as described in Examples 1 and 2. Saline was given to groups of control animals.

For i.m. immunization alternate left and right quadriceps were injected with 100 μg of DNA in 50 μl of PBS on three occasions at 0, 3 and 6 weeks. For i.n. immunization, anaesthetized mice aspirated 50 μl of PBS containing 50 μg DNA on three occasions at 0, 3 and 6 weeks. At week 8, immunized mice were inoculated i.n. with $5\times10^5$ IFU of *C. pneumoniae*, strain AR39 in 100 μl of SPG buffer to test their ability to limit the growth of a sublethal *C. pneumoniae* challenge.

Lungs were taken from mice at days 5 and 9 postchallenge and immediately homogenised in SPG buffer (7.5% sucrose, 5 mM glutamate, 12.5 mM phosphate pH7.5). The homogenate was stored frozen at −70° C. until assay. Dilutions of the homogenate were assayed for the presence of infectious chlamydia by inoculation onto monolayers of susceptible cells. The inoculum was centrifuged onto the cells at 300 rpm for 1 hour, then the cells were incubated for three days at 35° C. in the presence of 1 μg/ml cycloheximide. After incubation the monolayers were fixed with formalin and methanol then immunoperoxidase stained for the presence of chlamydial inclusions using convalescent sera from rabbits infected with *C. pneumoniae* and metal-enhanced DAB as a peroxidase substrate.

Figure 4:
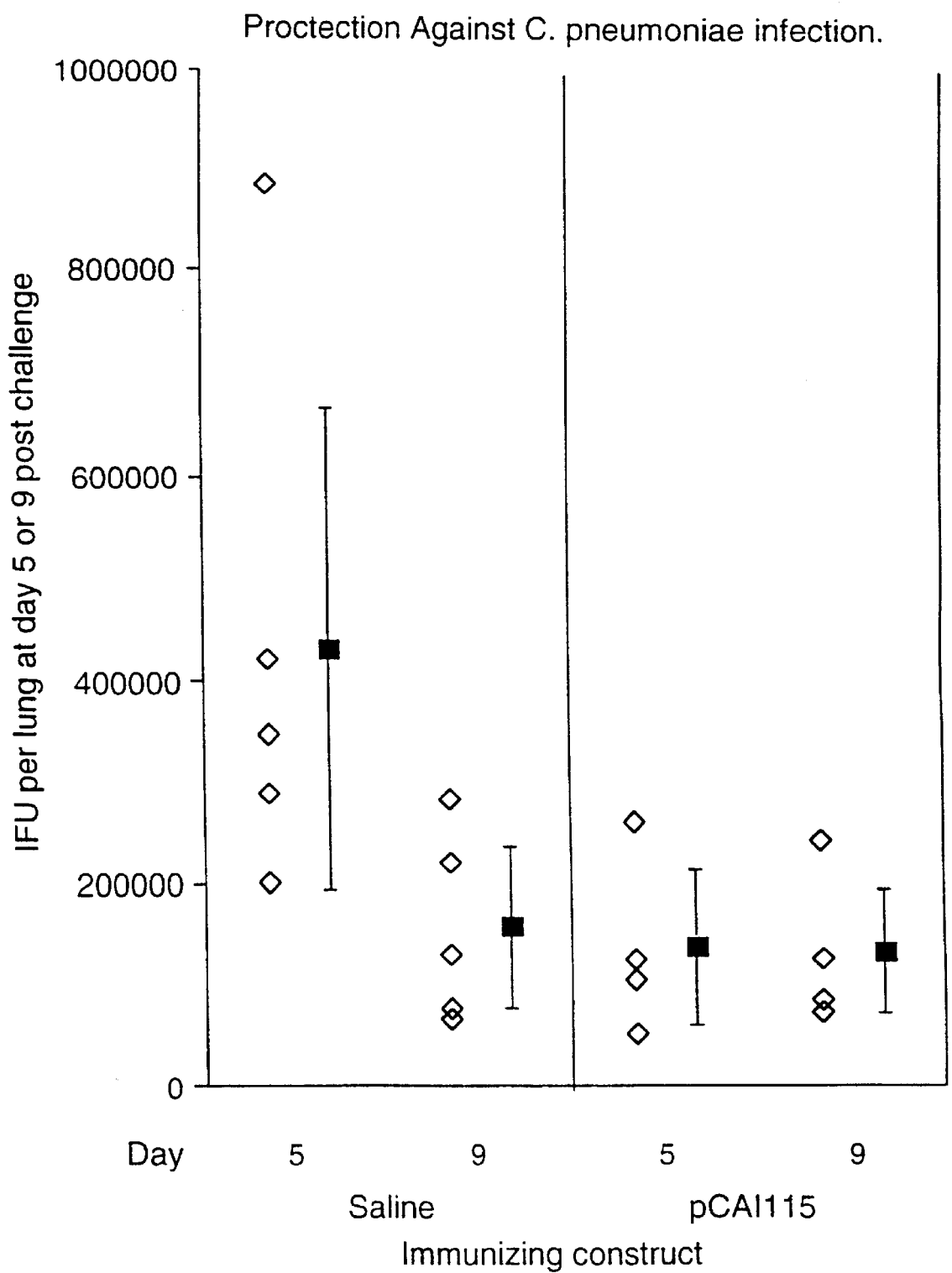
FIG. 4 illustrates protection against *C. pneumoniae* infection by pCAI115 following DNA immunization with pCAI115, in comparison to a saline control, wherein the individual data points (open diamonds) are shown for each animal, as well as the mean (solid squares) and standard deviation for each group.

FIG. 4 and Table 1 show that mice immunized i.n. and i.m. with pCAI115 had chlamydial lung titers less than 262,500 in 4 of 4 cases at day 5 and less than 250,000 in 4 of 4 cases at day 9 whereas the range of values for control mice sham immunized with saline was 202,400–886,800 IFU/lung (mean 429,800) at day 5 and 78,4000–284,600 IFU/lung (mean 157,080) at day 9.

TABLE 1

BACTERIAL LOAD (INCLUSION FORMING UNITS PER LUNG) IN THE LUNGS OF BALB/C MICE IMMUNIZED WITH VARIOUS DNA IMMUNIZATION CONSTRUCTS

IMMUNIZING CONSTRUCT

| MOUSE | Saline Day 5 | Saline Day 9 | pCAI115 Day 5 | pCAI115 Day 9 |
|---|---|---|---|---|
| 1 | 348200 | 68600 | 128000 | 244200 |
| 2 | 202400 | 262400 | 262400 | 75600 |
| 3 | 422400 | 132000 | 107000 | 127800 |
| 4 | 289200 | 78400 | 53600 | 86600 |
| 5 | 886800 | 221800 | | |
| MEAN | 429800 | 157080 | 137750 | 133550 |
| SD | 267881.24 | 93672.69 | 88805.912 | 77112.45 |

REFERENCES

1. Grayston et al. (1995) Journal of Infectious Diseases 168:1231.
2. Campos et al. (1995) Investigation of Ophthalmology and Visual Science 36:1477.
3. Grayston et al (1990) Journal of Infectious Diseases 161:618.
4. Marrie (1993) Clinical Infectious Diseases. 18:501.
5. Wang et al (1986) Chlamydial infections. Cambridge University Press, Cambridge. p. 329.
6. Norman et al., Acta Paediatrica, 1998, Vol 87, Iss 1, pp 23–27.
7. Saikku et al.(1988) Lancet;ii:983.
8. Thom et al. (1992) JAMA 268:68.
9. Linnanmaki et al. (1993), Circulation 87:1030.
10. Saikku et al. (1992)Annals internal Medicine 116:273.
11. Melnick et al(1993) American Journal of Medicine 95:499.
12. Shor et al. (1992) South African. Medical Journal 82:158.
13. Kuo et al. (1993) Journal of Infectious Diseases 167:841.
14. Kuo et al. (1993) Arteriosclerosis and Thrombosis 13:1500.
15. Campbell et al (1995) Journal of Infectious Diseases 172:585.
16. Chiu et al. Circulation, 1997 (In Press).
17. Ramirez et al (1996) Annals of Internal Medicine 125:979.
18. Jackson et al. Abst. K121, p272, 36th ICMC, Sep. 15–18, 1996, New Orleans.
19. Fong et al (1997) Journal of Clinical Microbiolology 35:48.
20. Hahn D L, et al. Evidence for Chlamydia pneunoniae infection in steroid-dependent asthma. Ann Allergy Asthma Immunol. January 1998; 80(1): 45–49.
21. Hahn D L, et al. Association of *Chlamydia pneumoniae* IgA antibodies with recently symptomatic asthma. Epidemiol Infect. December 1996; 117(3): 513–517.
22. Bjomsson E, et al. Serology of chiamydia in relation to asthma and bronchial hyperresponsiveness. Scand J Infect Dis. 1996; 28(1): 63–69.
23. Hahn D L. Treatment of *Chlamydia pneumoniae* infection in adult asthma: a before-after trial. J Fam Pract. October 1995; 41(4): 345–351.
24. Allegra L, et al. Acute exacerbations of asthma in adults: role of *Chlamydia pneumoniae* infection. Eur Respir J. December 1994; 7(12): 2165–2168.
25. Hahn D L, et al. Association of *Chlamydia pneumoniae* (strain TWAR) infection with wheezing, asthmatic bronchitis, and adult-onset asthma. JAMA. Jul. 10, 1999; 266(2): 225–230.
26. Pal et al. (1996) Infection and Immunity.64:5341.
27. Jones et al. (1995) Vaccine 13:715.
28. Igietsemes et al. (1993) Immunology 5:317.
29. lgietseme et al (1993) Regional Immunology 5:317.
30. Magee et al (1993) Regional Immunology 5:305.
31. Landers et al (1991) Infection & Immunity 59:3774.
32. Magee et al (1995) Infection & Immunity 63:516.
33. Cotter et al. (1995) Infection and immunity 63:4704.
34. Campbell et al (1990) Infection and Immunity 58:93.
35. McCafferty et al (1995) Infection and Immunity 63:2387–9.
36. Knudsen et al (1996)Third Meeting of the European Society for Chlamydia Research, Vienna.
37. Wiedmann-Al-Ahmad M, et al. Reactions of polyclonal and neutralizing anti-p54 monoclonal antibodies with an isolated, species-specific 54-kilodalton protein of *Chlamydia pneumoniae*. Clin Diagn Lab Immunol. November 1997; 4(6): 700–704.
38. Hughes etal., 1992. Infect. Immun. 60(9):3497.
39. Dion et a., 1990. Virology 179:474–477.
40. Snijders et al., 1991. J. Gen. Virol. 72:557–565.
41. Langeveld et al., Vaccine 12(15):1473–1480, 1994.
42. Ausubel et al., Current Protocols in Molecular Biology, John Wiley & Sons Inc., 1994.
43. Kunkel et al., Proc. Natl. Acad. Sci. USA (1985) 82:448.
44. Silhavy et al. Experiments with Gene Fusions, Cold Spring Harbor Laboratory Press, 1984.
45. Davis et al. A Manual for Genetic Engineering: Advanced Bacterial Genetics, Cold Spring Harbor Laboratory Press, 1980).
46. Casey & Davidson, Nucl. Acid Res. (1977) 4:1539.
47. Cagnon et al., Protein Engineering (1991) 4(7):843.
48. Takase et al., J. Bact. (1987) 169:5692.
49. Perez Melgosa et al., Infect Immun (1994) 62:880.
50. Watson et al., Nucleic Acids Res (1990) 18:5299.
51. Watson et al., Microbiology (1995) 141:2489.
52. Melgosa et al., FEMS Microbiol Lett (1993) 112:199.
53. Campbell et al., J Clin Microbiol (1990) 28:1261.
54. lijima et al., J Clin Microbiol (1994) 32:583.
54A. Tartaglia et al, Virology (1992)188:217.
55. Taylor et al, Vaccine (1995) 13:539.
56. Kieny et al., Nature (1994) 312:163.
57. Mekalanos et al., Nature (1983) 306:551.
58. Nakayama et al., Bio/Tech. (1988) 6:693.
59. High et al., EMBO (1992) 11:1991.
60. Sizemore et al., Science (1995) 270:299.
61. Medaglini et al., Pro. Nati. Acad. Sci. USA (1995) 92:6868.
62. Flynn J. L., Cell. Mol. Biol. (1994) 40 (suppl. I):31.
63. Norton & Coffin, Molec. Cell Biol. (1985) 5:281.
64. Li et al., Gene (1989) 78:243.
65. Li & Paulin, J. Biol. Chem. (1991) 266:6562.
66. Li & Paulin, J. Biol. Chem. (1993) 268:10403.
67. Hartikka et al., Huiman Gene Therapy (1996) 7:1205.

68. Tang et al., Nature (1992) 356:152.
69. Furth etal., Vaccine 1994,12:1503–1509.
70. Nielsen et al., Science (1991) 254:1497.
71. Southern, J. Mol. Biol. (1975) 98:503.
72. Dunn et al., Cell (1977) 12:23.
73. Towbin et al., Proc. Natl. Acad. Sci. USA (1779) 76:4350.
74. Laemmli, Nature (1970) 227:680.
75. Bachmaier et al., Science (1999) 283:1335.
76. Yang et al., 1993, Infection & Immunity, vol. 61, pp 2037–40.
77. Chi E. Y., Kuo C. C., Grayston J. T., 1987. Unique ultrastructure in the elementary body of Chlamydia sp strain TWAR. J. Bacteriol 169(8): 3757–63.
78. Needleman, S. B., and Wunsch, C. D. 1970, J. Mol Biol. 48:4434–53.
79. Sellers, P. H. 1974 On the theory and computation of evolutionary distances. J. Appl. Math(Siam) 26:787–793.
80. Waterman, M. S., Smith, T. F., and Beyer, W. A. 1976. Advan. Math. 20:367–387.
81. Smith, T. F., and Waterman, M. S. 1981 Identification of common molecular subsequences. J. Mol. Biol. 147:195–197.
82. Sobel, E. and Martinez, H. M. 1985 A Multiple Sequence Alignment Program. Nucleic Acid Res. 14:363–374.

What we claim is:

1. An expression cassette comprising an isolated nucleic acid molecule placed under the control of elements required for expression of said nucleic acid molecule, said isolated nucleic acid molecule comprising a polynucleotide sequence encoding an amino acid sequence selected from the group consisting of:

(a) an amino acid sequence as set forth in SEQ ID NO: 3; and (b) a fragment of the sequence in (a), said fragment comprising at least 12 amino acids and being capable of inducing an immune response against Chlamydia.

2. The expression cassette according to claim 1 wherein, in (b), said fragment comprises at least 20 amino acids.

3. The expression cassette according to claim 1 wherein, in (b), said fragment comprises at least 50 amino acids.

4. The expression cassette according to claim 1 wherein, in (b), said fragment comprises at least 75 amino acids.

5. The expression cassette according to claim 1 wherein, in (b), said fragment comprises at least 100 amino acids.

6. The expression cassette according to claim 1 wherein, in (b), said amino acid sequence retains the specific antigenicity of SEQ ID NO: 3.

7. The expression cassette according to claim 1, said nucleic acid molecule comprising a polynucleotide sequence encoding the amino acid sequence as set forth in SEQ ID NO: 3.

8. The expression cassette according to claim 1, wherein said polynucleotide sequence comprises the sequence set forth in SEQ ID NO: 1 or 2.

9. An expression vector comprising the expression cassette of claim 1.

10. A vaccine vector comprising an isolated nucleic acid molecule placed under the control of elements required for expression of said isolated nucleic acid molecule, said nucleic acid molecule comprising a polynucleotide sequence encoding an amino acid sequence selected from the group consisting of:

(a) an amino acid sequence as set forth in SEQ ID NO: 3; and (b) a fragment of the sequence in (a), said fragment comprising at least 12 amino acids and being capable of inducing an immune response against Chlamydia.

11. The vaccine vector according to claim 10 wherein, in (b), said fragment comprises at least 20 amino acids.

12. The vaccine vector according to claim 10 wherein, in (b), said fragment comprises at least 50 amino acids.

13. The vaccine vector according to claim 10 wherein, in (b), said fragment comprises at least 75 amino acids.

14. The vaccine vector according to claim 10 wherein, in (b), said fragment comprises at least 100 amino acids.

15. The vaccine vector according to claim 10 wherein, in (b), said amino acid sequence retains the specific antigenicity of SEQ ID NO: 3.

16. The vaccine vector according to claim 10, said nucleic acid molecule comprising a polynucleotide sequence encoding the amino acid sequence as set forth in SEQ ID NO: 3.

17. The vaccine vector according to claim 10, wherein said polynucleotide sequence comprises the sequence set forth in SEQ ID NO: 1 or 2.

18. The vaccine vector according to claim 10 wherein the elements required for expression include a promoter.

19. The vaccine vector according to claim 18 wherein the promoter is a cytomegalovirus promoter.

20. The vaccine vector according to claim 19, which is a plasmid vector.

21. The vaccine vector of claim 20 wherein said plasmid vector has the identifying characteristics of plasmid pCAI115, as shown in FIG. 3.

22. An imunogenic composition comprising an isolated nucleic acid molecule comprising a polynucleotide sequence encoding an amino acid sequence selected from the group consisting of:

(a) an amino acid sequence as set forth in SEQ ID NO: 3; and (b) a fragment of the sequence in (a), said fragment comprising at least 12 amino acids and being capable of inducing an immune response against Chlamydia.

23. An immunogenic composition comprising a vaccine vector according to claim 10.

24. An immunogenic composition comprising a vaccine vector according to claim 11.

25. An immunogenic composition comprising a vaccine vector according to claim 12.

26. An immunogenic composition comprising a vaccine vector according to claim 13.

27. An immunogenic composition comprising a vaccine vector according to claim 14.

28. An immunogenic composition comprising a vaccine vector according to claim 15.

29. An immunogenic composition comprising a vaccine vector according to claim 16.

30. An immunogenic composition comprising a vaccine vector according to claim 17.

31. A method for inducing an immune response against Chlamydia, comprising administering to a host an effective amount of an immunogenic composition according to claim 23.

32. A method for inducing an immune response against Chlamydia, comprising administering to a host an effective amount of an immunogenic composition according to claim 24.

33. A method for inducing an immune response against Chlamydia, comprising administering to a host an effective amount of an immunogenic composition according to claim 25.

34. A method for inducing an immune response against Chlamydia, comprising administering to a host an effective amount of an immunogenic composition according to claim 26.

35. A method for inducing an immune response against Chlamydia, comprising administering to a host an effective amount of an immunogenic composition according to claim 27.

36. A method for inducing an immune response against Chlamydia, comprising administering to a host an effective amount of an immunogenic composition according to claim 28.

37. A method for inducing an immune response against Chlamydia, comprising administering to a host an effective amount of an immunogenic composition according to claim 29.

38. A method for inducing an immune response against Chlamydia, comprising administering to a host an effective amount of an immunogenic composition according to claim 30.

* * * * *

SEQUENCE LISTING

<160> NUMBER OF SEQ ID NOS: 5

<210> SEQ ID NO 1
<211> LENGTH: 750
<212> TYPE: DNA
<213> ORGANISM: Chlamydia pneumoniae

<400> SEQUENCE: 1

```
aactctctaa ttaaaccgt  aattactgtc cgtacaacaa gataataagt aaaaaacaca      60
aaaaatagtg attttatgac ctcaccgatc cccttcagt  ctagtggcga tgcctctttc     120
cttgccgagc agccacagca actcccgtct acttctgaat ctcagctagt aactcaattg     180
ctaaccatga tgaagcatac tcaagcatta tccgaaacgg ttcttcaaca acaacgcgat     240
cgattaccaa ccgcatctat tatccttcaa gtaggaggag ctcctacagg aggagcgggt     300
gcgccttttc aaccaggacc ggcagatgat catcatcatc ccataccgcc gcctgttgta     360
ccagctcaaa tagaaacaga aatcaccact ataagatccg agttacagct catgcgatct     420
actctacaac aaagcacaaa aggagctcgt acaggagttc tagtggttac tgcaatctta     480
atgacgatct ccttattggc tattattatc ataatactag ctgtgcttgg atttacgggc     540
gtcttgcctc aagtagcttt attgatgcag ggtgaaacaa atctgatttg ggctatggtg     600
agcggttcta ttatttgctt tattgcgcta attggaactc taggattaat tttaacaaat     660
aagaacacgc ctctaccggc ttcttaaaaa aataaattga attagaataa gtaatagtaa     720
ttttcttcat acctcccttg caattaatca                                      750
```

<210> SEQ ID NO 2
<211> LENGTH: 609
<212> TYPE: DNA
<213> ORGANISM: Chlamydia pneumoniae

<400> SEQUENCE: 2

```
atgacctcac cgatcccctt tcagtctagt ggcgatgcct ctttccttgc cgagcagcca      60
cagcaactcc cgtctacttc tgaatctcag ctagtaactc aattgctaac catgatgaag     120
catactcaag cattatccga aacggttctt caacaacaac gcgatcgatt accaaccgca     180
tctattatcc ttcaagtagg aggagctcct acaggaggag cgggtgcgcc ttttcaacca     240
ggaccggcag atgatcatca tcatcccata ccgccgcctg ttgtaccagc tcaaatagaa     300
acagaaatca ccactataag atccgagtta cagctcatgc gatctactct acaacaaagc     360
acaaaggag  ctcgtacagg agttctagtg gttactgcaa tcttaatgac gatctcctta     420
```

-continued

```
ttggctatta ttatcataat actagctgtg cttggattta cgggcgtctt gcctcaagta    480
gctttattga tgcagggtga aacaaatctg atttgggcta tggtgagcgg ttctattatt    540
tgctttattg cgctaattgg aactctagga ttaattttaa caaataagaa cacgcctcta    600
ccggcttct                                                            609
```

<210> SEQ ID NO 3
<211> LENGTH: 203
<212> TYPE: PRT
<213> ORGANISM: Chlamydia pneumoniae

<400> SEQUENCE: 3

```
Met Thr Ser Pro Ile Pro Phe Gln Ser Ser Gly Asp Ala Ser Phe Leu
  1               5                  10                  15

Ala Glu Gln Pro Gln Gln Leu Pro Ser Thr Ser Glu Ser Gln Leu Val
                 20                  25                  30

Thr Gln Leu Leu Thr Met Met Lys His Thr Gln Ala Leu Ser Glu Thr
             35                  40                  45

Val Leu Gln Gln Gln Arg Asp Arg Leu Pro Thr Ala Ser Ile Ile Leu
         50                  55                  60

Gln Val Gly Gly Ala Pro Thr Gly Gly Ala Gly Ala Pro Phe Gln Pro
 65                  70                  75                  80

Gly Pro Ala Asp Asp His His His Pro Ile Pro Pro Val Val Pro
                 85                  90                  95

Ala Gln Ile Glu Thr Glu Ile Thr Thr Ile Arg Ser Glu Leu Gln Leu
                100                 105                 110

Met Arg Ser Thr Leu Gln Gln Ser Thr Lys Gly Ala Arg Thr Gly Val
            115                 120                 125

Leu Val Val Thr Ala Ile Leu Met Thr Ile Ser Leu Leu Ala Ile Ile
        130                 135                 140

Ile Ile Ile Leu Ala Val Leu Gly Phe Thr Val Leu Pro Gln Val
145                 150                 155                 160

Ala Leu Leu Met Gln Gly Glu Thr Asn Leu Ile Trp Ala Met Val Ser
                165                 170                 175

Gly Ser Ile Ile Cys Phe Ile Ala Leu Ile Gly Thr Leu Gly Leu Ile
                180                 185                 190

Leu Thr Asn Lys Asn Thr Pro Leu Pro Ala Ser
            195                 200
```

<210> SEQ ID NO 4
<211> LENGTH: 44
<212> TYPE: DNA
<213> ORGANISM: Chlamydia pneumoniae

<400> SEQUENCE: 4

```
ataagaatgc ggccgccacc atgacctcac cgatccccct tcag                      44
```

<210> SEQ ID NO 5
<211> LENGTH: 31
<212> TYPE: DNA
<213> ORGANISM: Chlamydia pneumoniae

<400> SEQUENCE: 5

```
gcgccggatc cgagaagccg gtagaggcgt g                                    31
```